United States Patent

Shundo et al.

Patent Number: 6,045,720
Date of Patent: Apr. 4, 2000

[54] PYRIDINE COMPOUND AND LIQUID CRYSTALLINE COMPOSITION

[75] Inventors: Ryushi Shundo; Shinichi Saito; Eiji Okabe; Hideo Saito, all of Ichihara, Japan

[73] Assignee: Chisso Corporation, Tokyo, Japan

[21] Appl. No.: 09/205,613

[22] Filed: Dec. 4, 1998

[30] Foreign Application Priority Data

Dec. 18, 1997 [JP] Japan .................................. 9-364608

[51] Int. Cl.$^7$ .......................... C09K 19/34; C07D 213/06
[52] U.S. Cl. .................... 252/299.61; 546/342; 546/326; 546/318; 546/314; 546/290
[58] Field of Search ................ 252/299.61; 546/342, 546/326, 318, 314, 290

[56] References Cited

U.S. PATENT DOCUMENTS 5,328,643  7/1994  Sudo et al. ........................ 252/299.65

Primary Examiner—John Kight
Assistant Examiner—Charanjit S. Aulakh
Attorney, Agent, or Firm—McDermott, Will & Emery

[57] ABSTRACT

A compound expressed by the following formula (1) and a liquid crystalline composition with using it are provided:

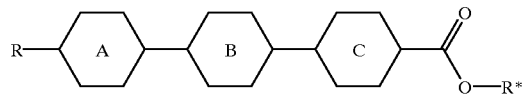

wherein, either one of rings A, B and C denotes

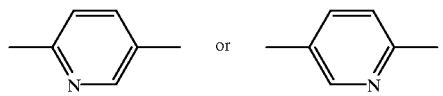

remaining two of them denote each independently

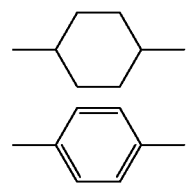

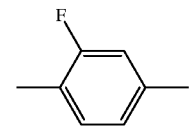
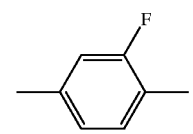
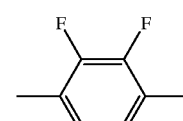
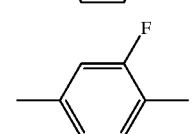
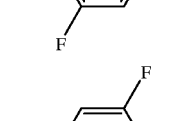
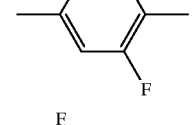
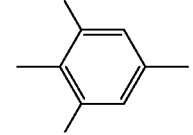

R denotes an alkyl group or an alkoxy group with 4–16 carbon atoms, R* denotes

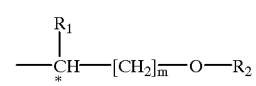

in which, $R_1$ denotes $CH_3$, $CF_3$, $CH_2F$ or $CHF_2$, $R_2$ denotes an alkyl group with 1–10 carbon atoms and m denotes 2–12.

The said compound exhibits a ferroelectric liquid crystalline phase and an antiferroelectric liquid crystalline phase by itself.

3 Claims, No Drawings

000
PYRIDINE COMPOUND AND LIQUID CRYSTALLINE COMPOSITION

FIELD OF THE INVENTION

The present invention relates to a novel liquid crystalline compound which is preferably useful for a liquid crystal display element and a liquid crystal optical switching element, a liquid crystalline composition containing the said compound as well as a liquid crystal display element which is made with using it.

In more detail, the invention relates to a novel optically active compound which is preferably useful for ferroelectric and antiferroelectric liquid crystal display elements, as well as a liquid crystalline composition and a display element constituted by using it.

BACKGROUND ART

Now, liquid crystal display elements are used widely. Among them, a TN (twist nematic) type display mode is most widely used as a low-grade display element. The said TN display mode has many advantages such as low driving voltage, low consumed electric power and so on. As to a response speed, however, it is much inferior to luminous type display elements such as cathode-ray tube, electroluminescense and plasma display elements.

Although a display volume for a liquid crystal display element has been improved eminently owing to development of the so-called STN display element which is a new type TN display element and its twist angle made 180°~270°, there is still a limit about the response speed thereof. Furthermore, display elements equipped with switching elements on respective pixels of the TN display elements have appeared recently on the stage of the market. Much of them are thin film transistor elements (abbreviated as TFT type), and they have occupied much of the market as liquid crystal elements with high density, high volume and full colors.

However, since the said mode has a high dependence property on a visual field angle, it is preferably used for a personal terminal but unsuitable for an all-directional display. With the object of compensating the disadvantage, there has been developed an in-plane driving (abbreviated as IPS driving) display mode which is superior in visual angle characteristic.

In spite of these improvements, there are generally mentioned disadvantages about an image size and a production costs for TFT display. Since TFT uses a semiconductor technique, the image size thereof has a limit of twenty inch order and a time division ability has also a limit of 1000 lines.

On the other hand, display elements with using ferroelectric liquid crystals or antiferroelectric liquid crystals have been actively developed.

As a ferroelectric liquid crystal display (SSFLC) mode of a surface stabilized type with using the former liquid crystals was proposed by N. A. Clark and S. T. Laggawall in 1980. The latter antiferroelectric liquid crystalline phase was found by Furukawa et al. in 1987 at first and tentatively named as a chiral smectic Y (SY*) phase (see Ferroelectronics, Vol 85, p451, 1998). Thereafter, Chandanni et al. proved that the said phase is an antiferroelectric liquid crystalline phase. (see Japanese Journal of Applied Physics, Vol 28, p1265, 1989).

Both are the display modes for dissolving a dependence property of displayed colors on a visual field angle including reversal of tone, which is an essential defect of TN type display. Furthermore, they are expected for decrease in an element preparation cost since displaying in cell structure for a simple matrix is possible even during high time division driving.

In ferroelectric liquid crystalline phase states, only two states are stable, wherein an inclining direction of liquid crystalline molecules is determined by an applied direction of an electric field. In sum, one of two states can be selected by polarity of voltage.

In the antiferroelectric liquid crystalline phase states, there is also the third state stable during non-applied period of an electric field in addition to the above-mentioned states for the ferroelectric liquid crystalline states. The said state during non-applied period of the electric field is the so-called antiferroelectric state.

The non-electric field state (the antiferroelectric state) is subject to phase transition to ferroelectric phase state by application of the electric field and returned to the antiferroelectric phase state by removal of electric field. Two stable positions (a bistable stae) are present during application of the electric field (a ferroelectric phase state), and only one stable position is present without the electric field (antiferroelectric phase state). Three states including them are utilized for switching.

Hitherto, it was said that switching properties between three states have sharp threshold properties and exhibit wide optical hysteresis. There have been, however, reported recently those without any clear threshold in phase transition due to the electric field of the ferroelectric-antiferroelectric state and also without any observed optical hysteresis (for example, Young Member Society for Liquid Crystalline Research, the third lecture meeting, S6-1 etc.).

Recently observed features thereof are that antiferroelectric liquid crystals have not any memory action in principle and that they are very preferable for trials to fill them into a TFT type cell having an accomplished manufacturing process now and apply active matrix driving. The feature that a clear threshold being not appeared means the possibility for display of all half gradations, which suggests realization of full color displays.

Combination of wide field visual angle properties of ferroelectric liquid crystals and antiferroelectric liquid crystals in the TFT structure is expected to dissolve the visual field angle dependence, which is the largest weak point of liquid crystals.

In the case that antiferroelectric liquid crystals are used for switching elements etc., particularly in the case that application for the above-mentioned TFT driving being conducted, driving voltage is required to be low. Driving voltage for IC used in practical TFT elements is about 5V, which could not be attained by the conventional ferroelectric liquid crystals and antiferroelectric liquid crystals hitherto. Although many compounds having antiferroelectric liquid crystal properties have been reported, there are few antiferroelectric liquid crystalline compositions having low driving voltages and enough wide active temperature ranges. It is caused by the fact that only few antiferroelectric liquid crystalline compounds for constituting the compositions having enough satisfied properties are present.

The subject solved by the present invention is to provide an antiferroelectric liquid crystalline compound suitable for low voltage driving, more preferably for TNT driving.

DISCLOSURE OF THE INVENTION

The present inventions relates to a compound expressed by the general formula (1)

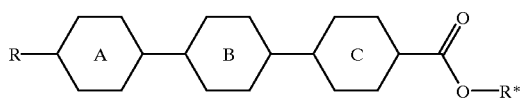

(wherein, either one of rings A, B and C denotes

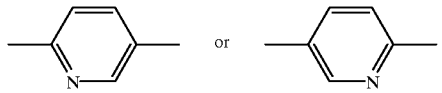

remaining two of them denote each independently

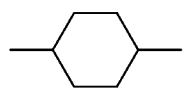

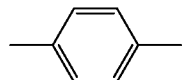

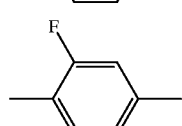

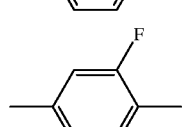

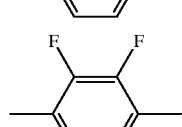

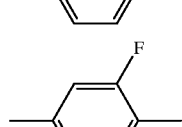

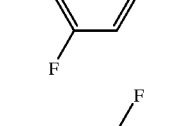

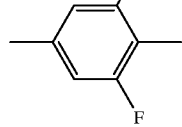

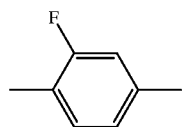

R denotes an alkyl group or an alkoxy group with 4–16 carbon atoms, and

R* denotes

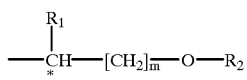

in which, $R_1$ denotes $CH_3$, $CF_3$, $CH_2F$ or $CHF_2$, $R_2$ denotes an alkyl group with 1–10 carbon atoms and m denotes 2–12); as well as a liquid crystalline composition and an element containing the said compound.

Backbone structures of the compounds according to the invention can be classified into the following six kinds with neglecting the existence of fluorine substitution.

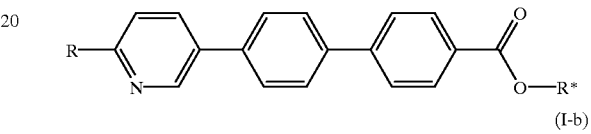
(I-a)

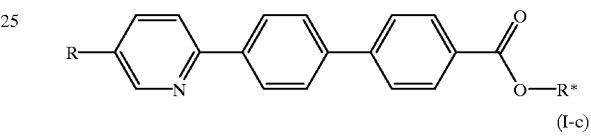
(I-b)

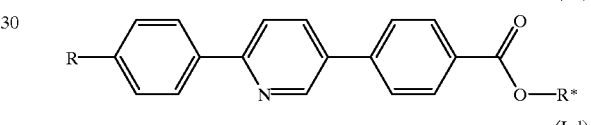
(I-c)

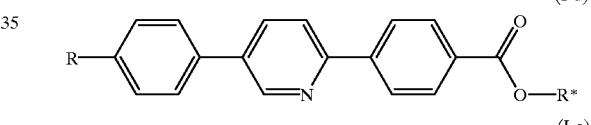
(I-d)

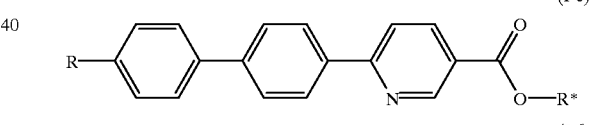
(I-e)

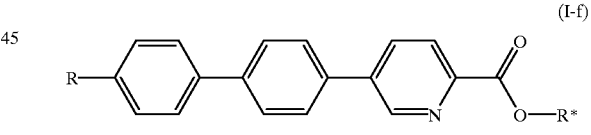
(I-f)

Furthermore, if fluorine substitution is taken in the consideration for a core structure, the following core structures are possible. That is, they are (I-a)–(I-f) structures themselves or those with one or more fluorine substituent (s), more preferably those unsubstituted or those with one or two fluorine substituent(s). Preferable structural examples are mentioned as follows.

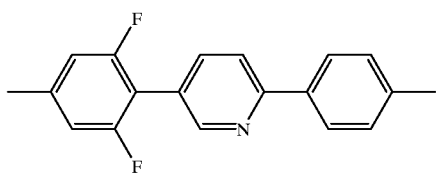

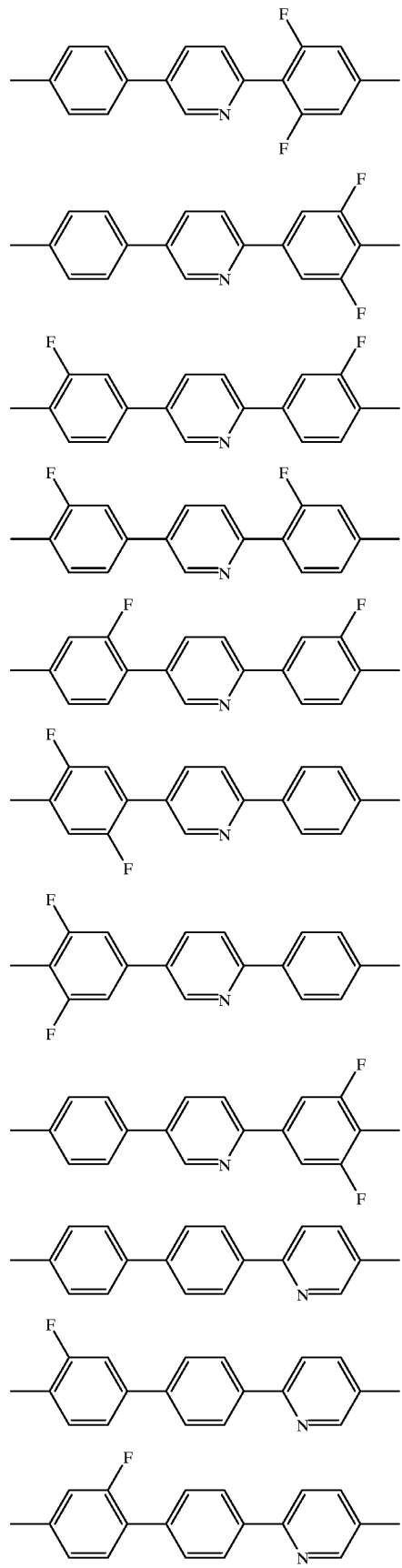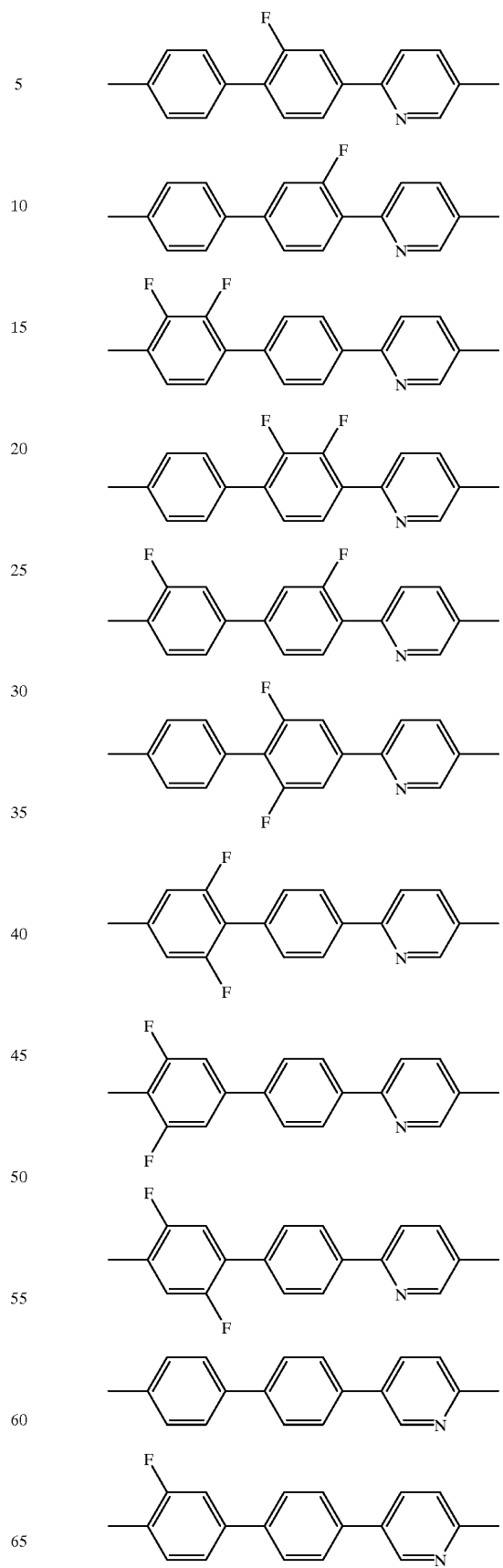

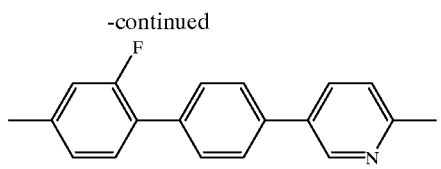

R in the formula (1) according to the invention is an alkyl group or an alkoxy group with 4–16 carbon atoms. More preferably, it is an alkyl group or an alkoxy group with 5–10 carbon atoms.

R* in the formula (1) according to the invention is

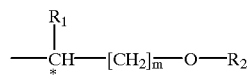

(wherein, $R_1$ denotes $CH_3$, $CF_3$, $CH_2F$ or $CHF_2$, $R_2$ denotes an alkyl group with 1–10 carbon atoms and m denotes 2–12).

Optically active alcohols corresponding to R* can be classified into the following (2-a)–(2-d) according to $R_1$.

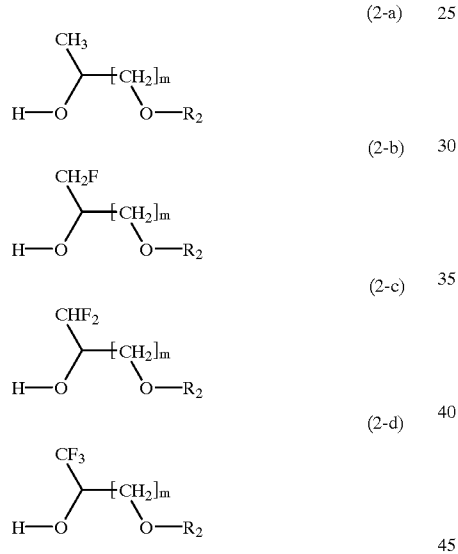

$R_2$ in the formula (1) according to the invention denotes an alkyl group with 1–10 carbon atoms, preferably an alkyl group particularly with 1–5 carbon atoms.

m is 2–12, more preferably 4–10, according to the invention.

In general, the liquid crystalline composition may be structured from a liquid crystalline compound or a liquid crystalline compound and a non-liquid crystalline compound. For the ferroelectric liquid crystalline composition according to the invention, there are mentioned the following methods; a method for structuring only from a ferroelectric liquid crystalline compound; and a method for obtaining a composition exhibiting a ferroelectric liquid crystalline phase totally by mixing one or more ferroelectric liquid crystalline compound(s) or non-liquid crystalline optically active compound(s) with a basic compound exhibiting aninclined smectic phase such as non-chiral smectic C, F, G, H, I and so on (hereinafter, abbreviated as Sc phase etc.) and a composition thereof.

In the case that the compound according to the invention being used alone or even in the case that the compound according to the invention being added to the basic material for obtaining the liquid crystalline composition with ferroelectric property totally, the compound according to the invention can express or induce a very high spontaneous polarization value.

Herein, a response time of ferroelectric liquid crystals is expressed by the following formula in principle.

$$\tau = \frac{\eta}{Ps \times E}$$

(wherein, $\tau$ denotes response time, $\eta$ denotes viscosity, Ps denotes spontaneous polarization, and E denotes applied voltage.)

Therefore, the high spontaneous polarization value is a necessary requirement for high-speed response.

The compound according to the invention can be preferably used as a component for a liquid crystalline display element having high-speed response.

There are exemplified the following backbone structures of basic materials suitable for structuring the ferroelectric liquid crystalline compositions by mixing with the optically active liquid crystalline compounds according to the invention.

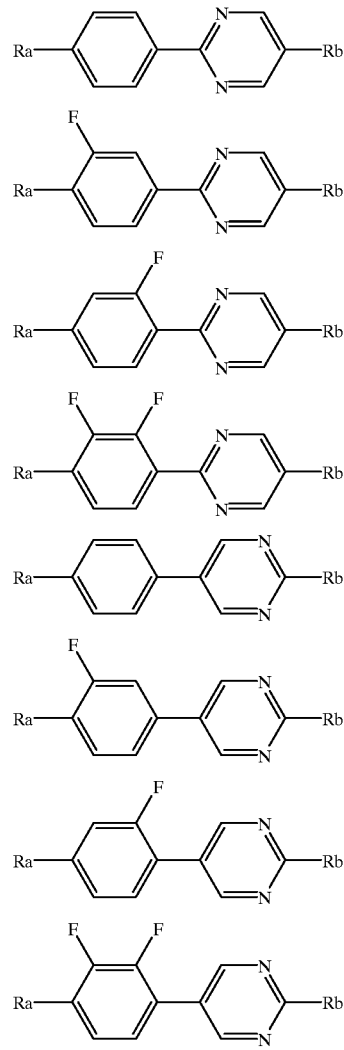

-continued
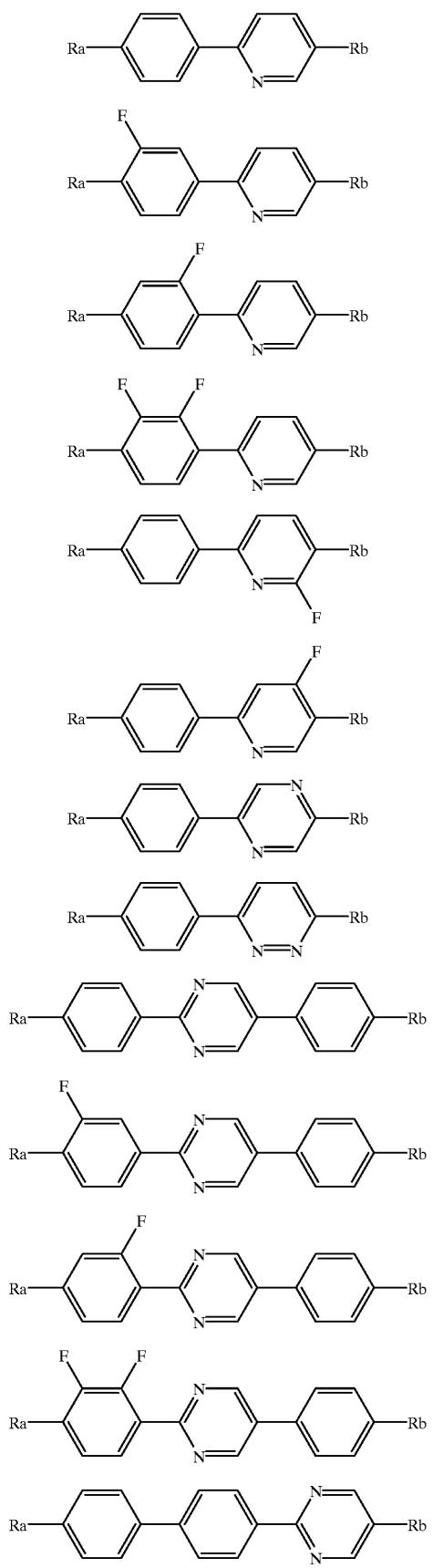
-continued
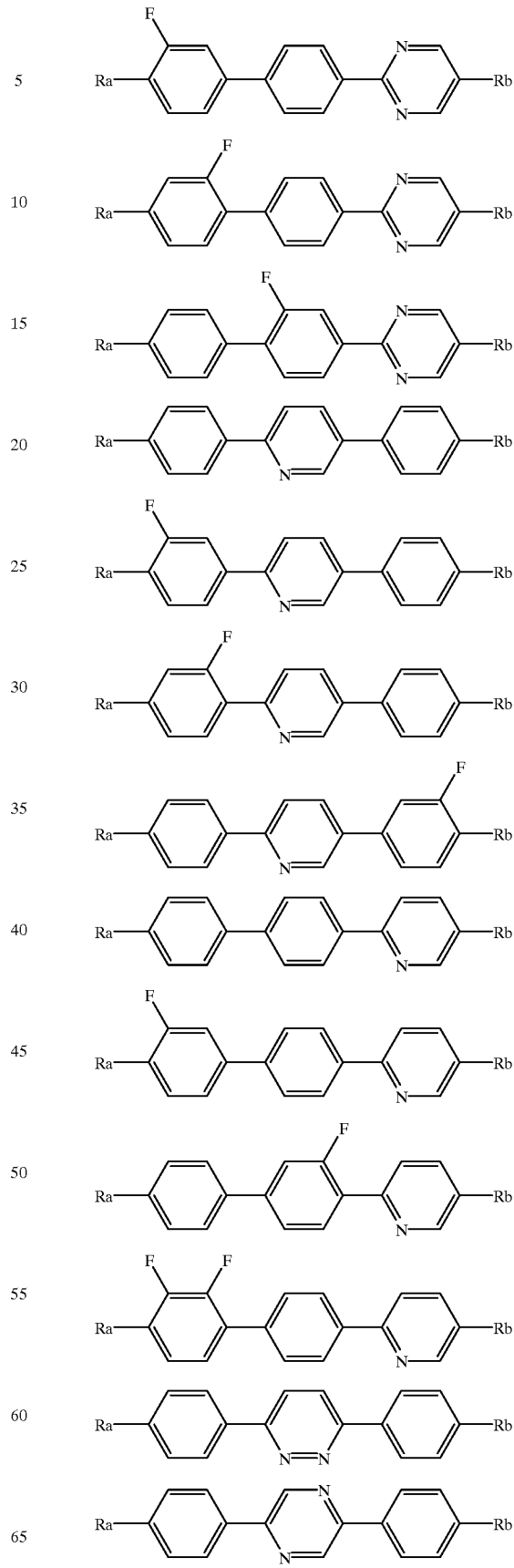

-continued

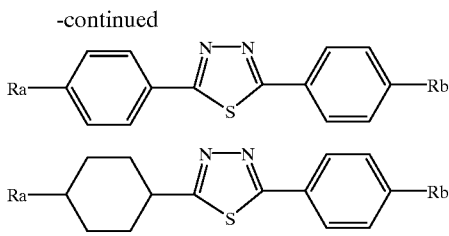

The compound according to the invention can be preferably used as a constituting component for the antiferroelectric liquid crystalline composition. The antiferroelectric liquid crystal element may be structured from the compound according to the invention alone or multiple compounds according to the invention. However, the said element cannot be obtained now by such a method for adding the optically active compound to the basic material similar to the case of the ferroelectric liquid crystalline composition. In other words, almost all constituting components of the antiferroelectric liquid crystalline composition are necessarily the antiferroelectric liquid crystalline compounds.

Therefore, the optically active compound for the antiferroelectric liquid crystal display is necessarily exhibit the antiferroelectric liquid crystal phase in a temperature range as wider as possible.

Structures of the compounds to be added to the compounds according to the invention for forming the antiferroelectric liquid crystalline compositions are shown as follows.

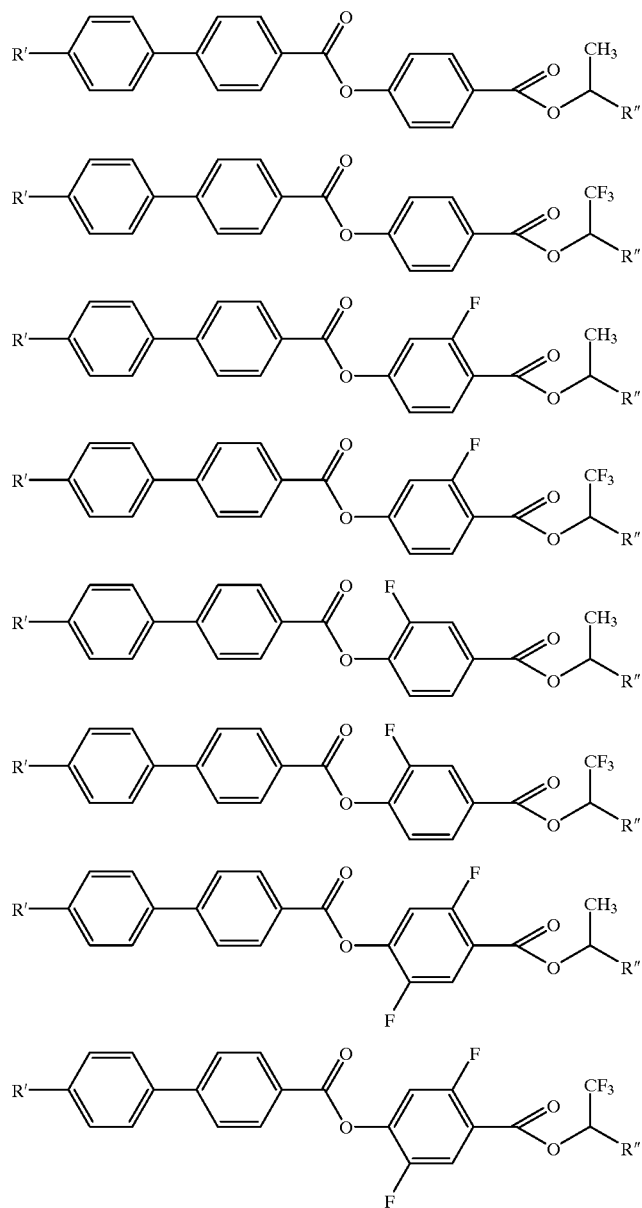

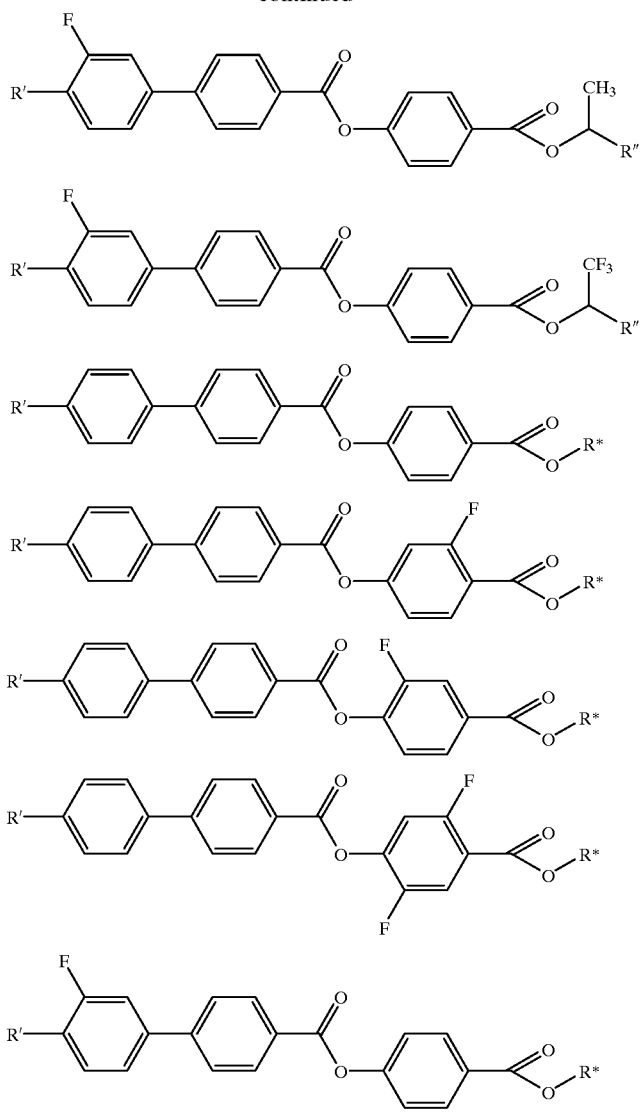

The present inventors have applied for patent about a liquid crystalline compound containing pyridine ring. Among them, there are mentioned the following ones having a three-ring structure as a core structure without any bonding group: Toku-Kai-Sho 64-63571

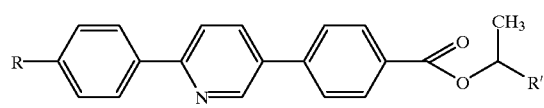

structure (a), and
Toku-Kai-Hei 5-271658

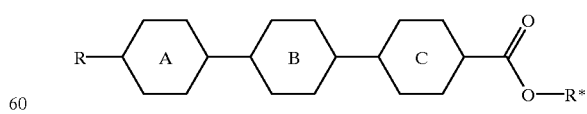

structure (b).
Furthermore, the following application had been made by the applicant other than the present applicant: Toku-Kai-Sho 64-71

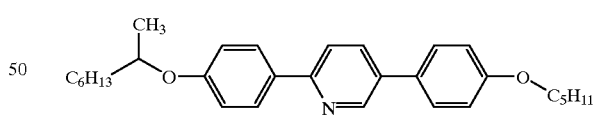

structure (c).
However, as to the ester structure of

R—A—B—C—C(=O)—O—R*

(wherein, definitions for rings A, B and C as well as R and R* are same as above),
only the structure (b) has been known and there is not any structure in which the optically active group is coincided with that claimed in the present application. Furthermore, the present inventors made application for the compound

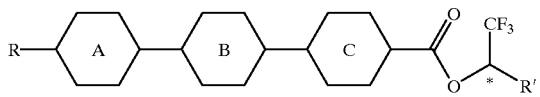

structure (d),
(wherein, R' is an alkyl group). (Toku-Gan-Hei 9-362040, application date: Dec. 11, 1997)

Among the compounds according to the present invention, more preferably used ones are exemplified as follows.

(1-trifluoromethyl-6-ethoxy)hexyl 4-(2-(4-butylphenyl) pyridin-5-yl)benzoate ester,
(1-trifluoromethyl-6-ethoxy)hexyl 4-(2-(4-pentylphenyl) pyridin-5-yl)benzoate ester,
(1-trifluoromethyl-6-ethoxy)hexyl 4-(2-(4-hexylphenyl) pyridin-5-yl)benzoate ester,
(1-trifluoromethyl-6-ethoxy)hexyl 4-(2-(4-heptylphenyl) pyridin-5-yl)benzoate ester,
(1-trifluoromethyl-6-ethoxy)hexyl 4-(2-(4-octylphenyl) pyridin-5-yl)benzoate ester,
(1-trifluoromethyl-6-ethoxy)hexyl 4-(2-(4-nonylphenyl) pyridin-5-yl)benzoate ester,
(1-trifluoromethyl-6-ethoxy)hexyl 4-(2-(4-decylphenyl) pyridin-5-yl)benzoate ester,
(1-trifluoromethyl-6-ethoxy)hexyl 4-(2-(4-undecylphenyl) pyridin-5-yl)benzoate ester,
(1-trifluoromethyl-6-ethoxy)hexyl 4-(2-(4-dodecylphenyl) pyridin-5-yl)benzoate ester,
(1-trifluoromethyl-6-ethoxy)hexyl 4-(2-(4-tridecylphenyl) pyridin-5-yl)benzoate ester,
(1-trifluoromethyl-6-ethoxy)hexyl 4-(2-(4-tetradecylphenyl) pyridin-5-yl)benzoate ester,
(1-trifluoromethyl-6-ethoxy)hexyl 4-(2-(4-pentadecylphenyl) pyridin-5-yl)benzoate ester,
(1-trifluoromethyl-6-ethoxy)hexyl 4-(2-(4-hexadecylphenyl) pyridin-5-yl)benzoate ester,
(1-trifluoromethyl-7-ethoxy)heptyl 4-(2-(4-butylphenyl) pyridin-5-yl)benzoate ester,
(1-trifluoromethyl-7-ethoxy)heptyl 4-(2-(4-pentylphenyl) pyridin-5-yl)benzoate ester,
(1-trifluoromethyl-7-ethoxy)heptyl 4-(2-(4-hexylphenyl) pyridin-5-yl)benzoate ester,
(1-trifluoromethyl-7-ethoxy)heptyl 4-(2-(4-heptylphenyl) pyridin-5-yl)benzoate ester,
(1-trifluoromethyl-7-ethoxy)heptyl 4-(2-(4-octylphenyl) pyridin-5-yl)benzoate ester,
(1-trifluoromethyl-7-ethoxy)heptyl 4-(2-(4-nonylphenyl) pyridin-5-yl)benzoate ester,
(1-trifluoromethyl-7-ethoxy)heptyl 4-(2-(4-decylphenyl) pyridin-5-yl)benzoate ester,
(1-trifluoromethyl-7-ethoxy)heptyl 4-(2-(4-undecylphenyl) pyridin-5-yl)benzoate ester,
(1-trifluoromethyl-7-ethoxy)heptyl 4-(2-(4-dodecylphenyl) pyridin-5-yl)benzoate ester,
(1-trifluoromethyl-7-ethoxy)heptyl 4-(2-(4-tridecylphenyl) pyridin-5-yl)benzoate ester,
(1-trifluoromethyl-7-ethoxy)heptyl 4-(2-(4-tetradecylphenyl) pyridin-5-yl)benzoate ester,
(1-trifluoromethyl-7-ethoxy)heptyl 4-(2-(4-pentadecylphenyl) pyridin-5-yl)benzoate ester,
(1-trifluoromethyl-7-ethoxy)heptyl 4-(2-(4-hexadecylphenyl) pyridin-5-yl)benzoate ester,
(1-trifluoromethyl-6-ethoxy)hexyl 4-(2-(4-butyloxyphenyl) pyridin-5-yl)benzoate ester,
(1-trifluoromethyl-6-ethoxy)hexyl 4-(2-(4-pentyloxyphenyl) pyridin-5-yl)benzoate ester,
(1-trifluoromethyl-6-ethoxy)hexyl 4-(2-(4-hexyloxyphenyl) pyridin-5-yl)benzoate ester,
(1-trifluoromethyl-6-ethoxy)hexyl 4-(2-(4-heptyloxyphenyl) pyridin-5-yl)benzoate ester,
(1-trifluoromethyl-6-ethoxy)hexyl 4-(2-(4-octyloxyphenyl) pyridin-5-yl)benzoate ester,
(1-trifluoromethyl-6-ethoxy)hexyl 4-(2-(4-nonyloxyphenyl) pyridin-5-yl)benzoate ester,
(1-trifluoromethyl-6-ethoxy)hexyl 4-(2-(4-decyloxyphenyl) pyridin-5-yl)benzoate ester,
(1-trifluoromethyl-6-ethoxy)hexyl 4-(2-(4-undecyloxyphenyl) pyridin-5-yl)benzoate ester,
(1-trifluoromethyl-6-ethoxy)hexyl 4-(2-(4-dodecyloxyphenyl) pyridin-5-yl)benzoate ester,
(1-trifluoromethyl-6-ethoxy)hexyl 4-(2-(4-tridecyloxyphenyl) pyridin-5-yl)benzoate ester,
(1-trifluoromethyl-6-ethoxy)hexyl 4-(2-(4-tetradecyloxyphenyl) pyridin-5-yl)benzoate ester,
(1-trifluoromethyl-6-ethoxy)hexyl 4-(2-(4-pentadecyloxyphenyl) pyridin-5-yl)benzoate ester,
(1-trifluoromethyl-6-ethoxy)hexyl 4-(2-(4-hexadecyloxyphenyl) pyridin-5-yl)benzoate ester,
(1-trifluoromethyl-7-ethoxy)heptyl 4-(2-(4-butyloxyphenyl) pyridin-5-yl)benzoate ester,
(1-trifluoromethyl-7-ethoxy)heptyl 4-(2-(4-pentyloxyphenyl) pyridin-5-yl)benzoate ester,
(1-trifluoromethyl-7-ethoxy)heptyl 4-(2-(4-hexyloxyphenyl) pyridin-5-yl)benzoate ester,
(1-trifluoromethyl-7-ethoxy)heptyl 4-(2-(4-heptyloxyphenyl) pyridin-5-yl)benzoate ester,
(1-trifluoromethyl-7-ethoxy)heptyl 4-(2-(4-octyloxyphenyl) pyridin-5-yl)benzoate ester,
(1-trifluoromethyl-7-ethoxy)heptyl 4-(2-(4-nonyloxyphenyl) pyridin-5-yl) benzoate ester,
(1-trifluoromethyl-7-ethoxy)heptyl 4-(2-(4-decyloxyphenyl) pyridin-5-yl)benzoate ester,
(1-trifluoromethyl-7-ethoxy)heptyl 4-(2-(4-undecyloxyphenyl) pyridin-5-yl)benzoate ester,
(1-trifluoromethyl-7-ethoxy)heptyl 4-(2-(4-dodecyloxyphenyl) pyridin-5-yl)benzoate ester,
(1-trifluoromethyl-7-ethoxy)heptyl 4-(2-(4-tridecyloxyphenyl) pyridin-5-yl)benzoate ester,
(1-trifluoromethyl-7-ethoxy)heptyl 4-(2-(4-tetradecyloxyphenyl) pyridin-5-yl)benzoate ester,
(1-trifluoromethyl-7-ethoxy)heptyl 4-(2-(4-pentadecyloxyphenyl) pyridin-5-yl)benzoate ester,
(1-trifluoromethyl-7-ethoxy)heptyl 4-(2-(4-hexadecyloxyphenyl) pyridin-5-yl)benzoate ester,
(1-trifluoromethyl-6-ethoxy)hexyl 4'-(5-butylpyridin-2-yl) biphenyl-4-yl carboxylate ester,
(1-trifluoromethyl-6-ethoxy)hexyl 4'-(5-pentylpyridin-2-yl) biphenyl-4-yl carboxylate ester,
(1-trifluoromethyl-6-ethoxy)hexyl 4'-(5-hexylpyridin-2-yl) biphenyl-4-yl carboxylate ester,
(1-trifluoromethyl-6-ethoxy)hexyl 4'-(5-heptylpyridin-2-yl) biphenyl-4-yl carboxylate ester,
(1-trifluoromethyl-6-ethoxy)hexyl 4'-(5-octylpyridin-2-yl) biphenyl-4-yl carboxylate ester,
(1-trifluoromethyl-6-ethoxy)hexyl 4'-(5-nonylpyridin-2-yl) biphenyl-4-yl carboxylate ester,
(1-trifluoromethyl-6-ethoxy)hexyl 4'-(5-decylpyridin-2-yl) biphenyl-4-yl carboxylate ester,
(1-trifluoromethyl-6-ethoxy)hexyl 4'-(5-undecylpyridin-2-yl) biphenyl-4-yl carboxylate ester,
(1-trifluoromethyl-6-ethoxy)hexyl 4'-(5-dodecylpyridin-2-yl) biphenyl-4-yl carboxylate ester,
(1-trifluoromethyl-6-ethoxy)hexyl 4'-(5-tridecylpyridin-2-yl) bi phenyl-4-yl carboxylate ester, (1-trifluoromethyl-6-ethoxy)hexyl 4'-(5-tetradecylpyridin-2-yl)biphenyl-4-yl carboxylate ester, (1-trifluoromethyl-6-ethoxy)hexyl 4'-(5-pentadecylpyridin-2-yl)biphenyl-4-yl carboxylate ester,
(1-trifluoromethyl-6-ethoxy)hexyl 4'-(5-hexadecylpyridin-2-yl) biphenyl-4-yl carboxylate ester,
(1-trifluoromethyl-7-ethoxy)heptyl 4'-(5-butylpyridin-2-yl) biphenyl-4-yl carboxylate ester,
(1-trifluoromethyl-7-ethoxy)heptyl 4'-(5-pentylpyridin-2-yl) biphenyl-4-yl carboxylate ester,
(1-trifluoromethyl-7-ethoxy)heptyl 4'-(5-hexylpyridin-2-yl) biphenyl-4-yl carboxylate ester,
(1-trifluoromethyl-7-ethoxy)heptyl 4'-(5-heptylpyridin-2-yl) biphenyl-4-yl carboxylate ester,
(1-trifluoromethyl-7-ethoxy)heptyl 4'-(5-octylpyridin-2-yl) biphenyl-4-yl carboxylate ester,
(1-trifluoromethyl-7-ethoxy)heptyl 4'-(5-nonylpyridin-2-yl) biphenyl-4-yl carboxylate ester,
(1-trifluoromethyl-7-ethoxy)heptyl 4'-(5-decylpyridin-2-yl) biphenyl-4-yl carboxylate ester,
(1-trifluoromethyl-7-ethoxy)heptyl 4'-(5-undecylpyridin-2-yl) biphenyl-4-yl carboxylate ester,
(1-trifluoromethyl-7-ethoxy)heptyl 4'-(5-dodecylpyridin-2-yl) biphenyl-4-yl carboxylate ester,
(1-trifluoromethyl-7-ethoxy)heptyl 4'-(5-tridecylpyridin-2-yl) biphenyl-4-yl carboxylate ester,
(1-trifluoromethyl-7-ethoxy)heptyl 4'-(5-tetradecylpyridin-2-yl)biphenyl-4-yl carboxylate ester,
(1-trifluoromethyl-7-ethoxy)heptyl 4'-(5-pentadecylpyridin-2-yl)biphenyl-4-yl carboxylate ester,
(1-trifluoromethyl-7-ethoxy)heptyl 4'-(5-hexadecylpyridin-2-yl) biphenyl-4-yl carboxylate ester,
(1-trifluoromethyl-6-ethoxy)hexyl 4'-(5-butyloxypyridin-2-yl) biphenyl-4-yl carboxylate ester,
(1-trifluoromethyl-6-ethoxy)hexyl 4'-(5-pentyloxypyridin-2-yl) biphenyl-4-yl carboxylate ester,
(1-trifluoromethyl-6-ethoxy)hexyl 4'-(5-hexyloxypyridin-2-yl) biphenyl-4-yl carboxylate ester,
(1-trifluoromethyl-6-ethoxy)hexyl 4'-(5-heptyloxypyridin-2-yl) biphenyl-4-yl carboxylate ester,
(1-trifluoromethyl-6-ethoxy)hexyl 4'-(5-octyloxypyridin-2-yl) biphenyl-4-yl carboxylate ester,
(1-trifluoromethyl-6-ethoxy)hexyl 4'-(5-nonyloxypyridin-2-yl) biphenyl-4-yl carboxylate ester,
(1-trifluoromethyl-6-ethoxy)hexyl 4'-(5-decyloxypyridin-2-yl) biphenyl-4-yl carboxylate ester,
(1-trifluoromethyl-6-ethoxy)hexyl 4'-(5-undecyloxypyridin-2-yl) biphenyl-4-yl carboxylate ester,
(1-trifluoromethyl-6-ethoxy)hexyl 4'-(5-dodecyloxypyridin-2-yl) biphenyl-4-yl carboxylate ester,
(1-trifluoromethyl-6-ethoxy)hexyl 4'-(5-tridecyloxypyridin-2-yl) biphenyl-4-yl carboxylate ester,
(1-trifluoromethyl-6-ethoxy)hexyl 4'-(5-tetradecyloxypyridin-2-yl)biphenyl-4-yl carboxylate ester,
(1-trifluoromethyl-6-ethoxy)hexyl 4'-(5-pentadecyloxypyridin-2-yl) biphenyl-4-yl carboxylate ester,
(1-trifluoromethyl-6-ethoxy)hexyl 4'-(5-hexadecyloxypyridin-2-yl)biphenyl-4-yl carboxylate ester,
(1-trifluoromethyl-7-ethoxy)heptyl 4'-(5-butyloxypyridin-2-yl) biphenyl-4-yl carboxylate ester,
(1-trifluoromethyl-7-ethoxy)heptyl 4'-5-pentyloxypyridin-2-yl) biphenyl-4-yl carboxylate ester,
(1-trifluoromethyl-7-ethoxy)heptyl 4'-(5-hexyloxypyridin-2-yl) biphenyl-4-yl carboxylate ester,
(1-trifluoromethyl-7-ethoxy)heptyl 4'-(5-heptyloxypyridin-2-yl) biphenyl-4-yl carboxylate ester,
(1-trifluoromethyl-7-ethoxy)heptyl 4'-(5-octyloxypyridin-2-yl) biphenyl-4-yl carboxylate ester,
(1-trifluoromethyl-7-ethoxy)heptyl 4'-(5-nonyloxypyridin-2-yl) biphenyl-4-yl carboxylate ester,
(1-trifluoromethyl-7-ethoxy)heptyl 4'-(5-decyloxypyridin-2-yl) biphenyl-4-yl carboxylate ester,
(1-trifluoromethyl-7-ethoxy)heptyl 4'-(5-undecyloxypyridin-2-yl) biphenyl-4-yl carboxylate ester,
(1-trifluoromethyl-7-ethoxy)heptyl 4'-(5-dodecyloxypyridin-2-yl) biphenyl-4-yl carboxylate ester,
(1-trifluoromethyl-7-ethoxy)heptyl 4'-(5-tridecyloxypyridin-2-yl)biphenyl-4-yl carboxylate ester,
(1-trifluoromethyl-7-ethoxy)heptyl 4'-(5-tetradecyloxypyridin-2-yl)biphenyl-4-yl carboxylate ester,
(1-trifluoromethyl-7-ethoxy)heptyl 4'-(5-pentadecyloxypyridin-2-yl)biphenyl-4-yl carboxylate ester,
(1-trifluoromethyl-7-ethoxy)heptyl 4'-(5-hexadecyloxypyridin-2-yl)biphenyl-4-yl carboxylate ester,
(1-trifluoromethyl-6-ethoxy)hexyl 4'-(2-butylpyridin-5-yl) biphenyl-4-yl carboxylate ester,
(1-trifluoromethyl-6-ethoxy)hexyl 4'-(2-pentylpyridin-5-yl) biphenyl-4-yl carboxylate ester,
(1-trifluoromethyl-6-ethoxy)hexyl 4'-(2-hexylpyridin-5-yl) biphenyl-4-yl carboxylate ester,
(1-trifluoromethyl-6-ethoxy)hexyl 4'-(2-heptylpyridin-5-yl) biphenyl-4-yl carboxylate ester,
(1-trifluoromethyl-6-ethoxy)hexyl 4'-(2-octylpyridin-5-yl) biphenyl-4-yl carboxylate ester,
(1-trifluoromethyl-6-ethoxy)hexyl 4'-(2-nonylpyridin-5-yl) biphenyl-4-yl carboxylate ester,
(1-trifluoromethyl-6-ethoxy)hexyl 4'-(2-decylpyridin-5-yl) biphenyl-4-yl carboxylate ester,
(1-trifluoromethyl-6-ethoxy)hexyl 4'-(2-undecylpyridin-5-yl) biphenyl-4-yl carboxylate ester,
(1-trifluoromethyl-6-ethoxy)hexyl 4'-(2-dodecylpyridin-5-yl) biphenyl-4-yl carboxylate ester,
(1-trifluoromethyl-6-ethoxy)hexyl 4'-(2-tridecylpyridin-5-yl) biphenyl-4-yl carboxylate ester,
(1-trifluoromethyl-6-ethoxy)hexyl 4'-(2-tetradecylpyridin-5-yl)biphenyl-4-yl carboxylate ester,
(1-trifluoromethyl-6-ethoxy)hexyl 4'-(2-pentadecylpyridin-5-yl)biphenyl-4-yl carboxylate ester,
(1-trifluoromethyl-6-ethoxy)hexyl 4'-(2-hexadecylpyridin-5-yl) biphenyl-4-yl carboxylate ester,
(1-trifluoromethyl-7-ethoxy)heptyl 4'-(2-butylpyridin-5-yl) biphenyl-4-yl carboxylate ester,
(1-trifluoromethyl-7-ethoxy)heptyl 4'-(2-pentylpyridin-5-yl) biphenyl-4-yl carboxylate ester,
(1-trifluoromethyl-7-ethoxy)heptyl 4'-(2-hexylpyridin-5-yl) biphenyl-4-yl carboxylate ester,
(1-trifluoromethyl-7-ethoxy)heptyl 4'-(2-heptylpyridin-5-yl) biphenyl-4-yl carboxylate ester,
(1-trifluoromethyl-7-ethoxy)heptyl 4'-(2-octylpyridin-5-yl) biphenyl-4-yl carboxylate ester,
(1-trifluoromethyl-7-ethoxy)heptyl 4'-(2-nonylpyridin-5-yl) biphenyl-4-yl carboxylate ester,
(1-trifluoromethyl-7-ethoxy)heptyl 4'-(2-decylpyridin-5-yl) biphenyl-4-yl carboxylate ester,
(1-trifluoromethyl-7-ethoxy)heptyl 4'-(2-undecylpyridin-5-yl) biphenyl-4-yl carboxylate ester,
(1-trifluoromethyl-7-ethoxy)heptyl 4'-(2-dodecylpyridin-5-yl) biphenyl-4-yl carboxylate ester, (1-trifluoromethyl-7-ethoxy)heptyl 4'-(2-tridecylpyridin-5-yl) biphenyl-4-yl carboxylate ester,
(1-trifluoromethyl-7-ethoxy)heptyl 4'-(2-tetradecylpyridin-5-yl)biphenyl-4-yl carboxylate ester,
(1-trifluoromethyl-7-ethoxy)heptyl 4'-(2-pentadecylpyridin-5-yl)biphenyl-4-yl carboxylate ester,
(1-trifluoromethyl-7-ethoxy)heptyl 4'-(2-hexadecylpyridin-5-yl) biphenyl-4-yl carboxylate ester,
(1-trifluoromethyl-6-ethoxy)hexyl 4'-(2-butyloxypyridin-5-yl) biphenyl-4-yl carboxylate ester,
(1-trifluoromethyl-6-ethoxy)hexyl 4'-(2-pentyloxypyridin-5-yl) biphenyl-4-yl carboxylate ester,
(1-trifluoromethyl-6-ethoxy)hexyl 4'-(2-hexyloxypyridin-5-yl) biphenyl-4-yl carboxylate ester,
(1-trifluoromethyl-6-ethoxy)hexyl 4'-(2-heptyloxypyridin-5-yl) biphenyl-4-yl carboxylate ester,
(1-trifluoromethyl-6-ethoxy)hexyl 4'-(2-octyloxypyridin-5-yl) biphenyl-4-yl carboxylate ester,
(1-trifluoromethyl-6-ethoxy)hexyl 4'-(2-nonyloxypyridin-5-yl) biphenyl-4-yl carboxylate ester,
(1-trifluoromethyl-6-ethoxy)hexyl 4'-(2-decyloxypyridin-5-yl) biphenyl-4-yl carboxylate ester,
(1-trifluoromethyl-6-ethoxy)hexyl 4'-(2-undecyloxypyridin-5-yl)biphenyl-4-yl carboxylate ester,
(1-trifluoromethyl-6-ethoxy)hexyl 4'-(2-dodecyloxypyridin-5-yl)biphenyl-4-yl carboxylate ester,
(1-trifluoromethyl-6-ethoxy)hexyl 4'-(2-tridecyloxypyridin-5-yl)biphenyl-4-yl carboxylate ester,
(1-trifluoromethyl-6-ethoxy)hexyl 4'-(2-tetradecyloxypyridin-5-yl)biphenyl-4-yl carboxylate ester,
(1-trifluoromethyl-6-ethoxy)hexyl 4'-(2-pentadecyloxypyridin-5-yl) biphenyl-4-yl carboxylate ester,
(1-trifluoromethyl-6-ethoxy)hexyl 4'-(2-hexadecyloxypyridin-5-yl)biphenyl-4-yl carboxylate ester,
(1-trifluoromethyl-7-ethoxy)heptyl 4'-(2-butyloxypyridin-5-yl) biphenyl-4-yl carboxylate ester,
(1-trifluoromethyl-7-ethoxy)heptyl 4'-(2-pentyloxypyridin-5-yl) biphenyl-4-yl carboxylate ester,
(1-trifluoromethyl-7-ethoxy)heptyl 4'-(2-hexyloxypyridin-5-yl) biphenyl-4-yl carboxylate ester,
(1-trifluoromethyl-7-ethoxy)heptyl 4'-(2-heptyloxypyridin-5-yl) biphenyl-4-yl carboxylate ester,
(1-trifluoromethyl-7-ethoxy)heptyl 4'-(2-octyloxypyridin-5-yl) biphenyl-4-yl carboxylate ester,
(1-trifluoromethyl-7-ethoxy)heptyl 4'-(2-nonyloxypyridin-5-yl) biphenyl-4-yl carboxylate ester,
(1-trifluoromethyl-7-ethoxy)heptyl 4'-(2-decyloxypyridin-5-yl) biphenyl-4-yl carboxylate ester,
(1-trifluoromethyl-7-ethoxy)heptyl 4'-(2-undecyloxypyridin-5-yl)biphenyl-4-yl carboxylate ester,
(1-trifluoromethyl-7-ethoxy)heptyl 4'-(2-dodecyloxypyridin-5-yl) biphenyl-4-yl carboxylate ester,
(1-trifluoromethyl-7-ethoxy)heptyl 4'-(2-tridecyloxypyridin-5-yl) biphenyl-4-yl carboxylate ester,
(1-trifluoromethyl-7-ethoxy)heptyl 4'-(2-tetradecyloxypyridin-5-yl)biphenyl-4-yl carboxylate ester,
(1-trifluoromethyl-7-ethoxy)heptyl 4'-(2-pentadecyloxypyridin-5-yl)biphenyl-4-yl carboxylate ester,
(1-trifluoromethyl-7-ethoxy)heptyl 4'-(2-hexadecyloxypyridin-5-yl)biphenyl-4-yl carboxylate ester,
(1-trifluoromethyl-6-ethoxy)hexyl 4-(5-(4-butylphenyl) pyridin-2-yl) benzoate ester,
(1-trifluoromethyl-6-ethoxy)hexyl 4-(5-(4-pentylphenyl) pyridin-2-yl) benzoate ester,
(1-trifluoromethyl-6-ethoxy)hexyl 4-(5-(4-hexylphenyl) pyridin-2-yl)benzoate ester,
(1-trifluoromethyl-6-ethoxy)hexyl 4-(5-(4-heptylphenyl) pyridin-2-yl)benzoate ester,
(1-trifluoromethyl-6-ethoxy)hexyl 4-(5-(4-octylphenyl) pyridin-2-yl)benzoate ester,
(1-trifluoromethyl-6-ethoxy)hexyl 4-(5-(4-nonylphenyl) pyridin-2-yl)benzoate ester,
(1-trifluoromethyl-6-ethoxy)hexyl 4-(5-(4-decylphenyl) pyridin-2-yl)benzoate ester,
(1-trifluoromethyl-6-ethoxy)hexyl 4-(5-(4-undecylphenyl) pyridin-2-yl)benzoate ester,
(1-trifluoromethyl-6-ethoxy)hexyl 4-(5-(4-dodecylphenyl) pyridin-2-yl)benzoate ester,
(1-trifluoromethyl-6-ethoxy)hexyl 4-(5-(4-tridecylphenyl) pyridin-2-yl)benzoate ester,
(1-trifluoromethyl-6-ethoxy)hexyl 4-(5-(4-tetradecylphenyl) pyridin-2-yl)benzoate ester,
(1-trifluoromethyl-6-ethoxy)hexyl 4-(5-(4-pentadecylphenyl) pyridin-2-yl)benzoate ester,
1-trifluoromethyl-6-ethoxy)hexyl 4-(5-(4-hexadecylphenyl) pyridin-2-yl)benzoate ester,
(1-trifluoromethyl-7-ethoxy)heptyl 4-(5-(4-butylphenyl) pyridin-2-yl)benzoate ester,
(1-trifluoromethyl-7-ethoxy)heptyl 4-(5-(4-pentylphenyl) pyridin-2-yl)benzoate ester,
(1-trifluoromethyl-7-ethoxy)heptyl 4-(5-(4-hexylphenyl) pyridin-2-yl)benzoate ester,
(1-trifluoromethyl-7-ethoxy)heptyl 4-(5-(4-heptylphenyl) pyridin-2-yl)benzoate ester,
(1-trifluoromethyl-7-ethoxy)heptyl 4-(5-(4-octylphenyl) pyridin-2 -yl)benzoate ester,
(1-trifluoromethyl-7-ethoxy)heptyl 4-(5-(4-nonylphenyl) pyridin-2-yl)benzoate ester,
(1-trifluoromethyl-7-ethoxy)heptyl 4-(5-(4-decylphenyl) pyridin-2-yl)benzoate ester,
(1-trifluoromethyl-7-ethoxy)heptyl 4-(5-(4-undecylphenyl) pyridin-2-yl)benzoate ester,
(1-trifluoromethyl-7-ethoxy)heptyl 4-(5-(4-dodecylphenyl) pyridin-2-yl)benzoate ester,
(1-trifluoromethyl-7-ethoxy)heptyl 4-(5-(4-tridecylphenyl) pyridin-2-yl)benzoate ester,
(1-trifluoromethyl-7-ethoxy)heptyl 4-(5-(4-tetradecylphenyl) pyridin-2-yl)benzoate ester,
(1-trifluoromethyl-7-ethoxy)heptyl 4-(5-(4-pentadecylphenyl) pyridin-2-yl)benzoate ester,
(1-trifluoromethyl-7-ethoxy)heptyl 4-(5-(4-hexadecylphenyl) pyridin-2-yl)benzoate ester,
(1-trifluoromethyl-6-ethoxy)hexyl 4-(5-(4-butyloxyphenyl) pyridin-2-yl)benzoate ester,
(1-trifluoromethyl-6-ethoxy)hexyl 4-(5-(4-pentyloxyphenyl) pyridin-2-yl)benzoate ester,
(1-trifluoromethyl-6-ethoxy)hexyl 4-(5-(4-hexyloxyphenyl) pyridin-2-yl)benzoate ester,
(1-trifluoromethyl-6-ethoxy)hexyl 4-(5-(4-heptyloxyphenyl) pyridin-2-yl)benzoate ester,
(1-trifluoromethyl-6-ethoxy)hexyl 4-(5-(4-octyloxyphenyl) pyridin-2-yl)benzoate ester,
(1-trifluoromethyl-6-ethoxy)hexyl 4-(5-(4-nonyloxyphenyl) pyridin-2-yl)benzoate ester,
(1-trifluoromethyl-6-ethoxy)hexyl 4-(5-(4-decyloxyphenyl) pyridin-2-yl)benzoate ester,
(1-trifluoromethyl-6-ethoxy)hexyl 4-(5-(4-undecyloxyphenyl) pyridin-2-yl)benzoate ester, (1-trifluoromethyl-6-ethoxy)hexyl 4-(5-(4-dodecyloxyphenyl) pyridin-2-yl)benzoate ester,
(1-trifluoromethyl-6-ethoxy)hexyl 4-(5-(4-tridecyloxyphenyl) pyridin-2-yl)benzoate ester,
(1-trifluoromethyl-6-ethoxy)hexyl 4-(5-(4-tetradecyloxyphenyl) pyridin-2-yl)benzoate ester,
(1-trifluoromethyl-6-ethoxy)hexyl 4-(5-(4-pentadecyloxyphenyl) pyridin-2-yl)benzoate ester,
(1-trifluoromethyl-6-ethoxy)hexyl 4-(5-(4-hexadecyloxyphenyl) pyridin-2-yl)benzoate ester,
(1-trifluoromethyl-7-ethoxy)heptyl 4-(5-(4-butyloxyphenyl) pyridin-2-yl)benzoate ester,
(1-trifluoromethyl-7-ethoxy)heptyl 4-(5-(4-pentyloxyphenyl) pyridin-2-yl)benzoate ester,
(1-trifluoromethyl-7-ethoxy)heptyl 4-(5-(4-hexyloxyphenyl) pyridin-2-yl)benzoate ester,
(1-trifluoromethyl-7-ethoxy)heptyl 4-(5-(4-heptyloxyphenyl) pyridin-2-yl)benzoate ester,
(1-trifluoromethyl-7-ethoxy)heptyl 4-(5-(4-octyloxyphenyl) pyridin-2-yl)benzoate ester,
(1-trifluoromethyl-7-ethoxy)heptyl 4-(5-(4-nonyloxyphenyl) pyridin-2-yl)benzoate ester,
(1-trifluoromethyl-7-ethoxy)heptyl 4-(5-(4-decyloxyphenyl) pyridin-2-yl)benzoate ester,
(1-trifluoromethyl-7-ethoxy)heptyl 4-(5-(4-undecyloxyphenyl) pyridin-2-yl)benzoate ester,
(1-trifluoromethyl-7-ethoxy)heptyl 4-(5-(4-dodecyloxyphenyl) pyridin-2-yl)benzoate ester,
(1-trifluoromethyl-7-ethoxy)heptyl 4-(5-(4-tridecyloxyphenyl) pyridin-2-yl)benzoate ester,
(1-trifluoromethyl-7-ethoxy)heptyl 4-(5-(4-tetradecyloxyphenyl) pyridin-2-yl)benzoate ester,
(1-trifluoromethyl-7-ethoxy)heptyl 4-(5-(4-pentadecyloxyphenyl) pyridin-2-yl)benzoate ester,
(1-trifluoromethyl-7-ethoxy)heptyl 4-(5-(4-hexadecyloxyphenyl) pyridin-2-yl)benzoate ester, Preparation of the compound The general method for preparing the compound according to the invention will be illustrated as follows.

It was mentioned above that the compound according to the invention can be classified into six core structures of (1-a)–(1-f) disregard of the existence of fluorine substitution.

In the case of (1-a), those having the core structure of (1-a) can be prepared preferably by the following step.

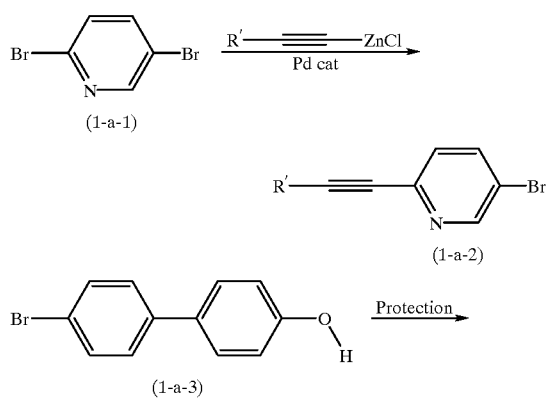

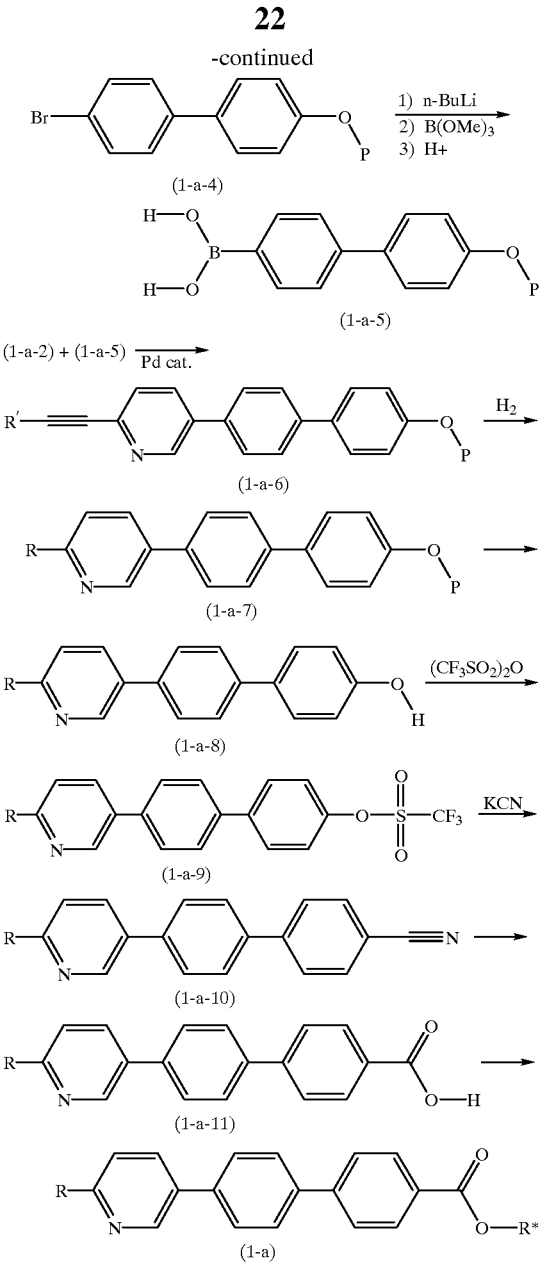

That is, an alkynylzinc reagent is reacted with 2,5-dibromopyridine (1-a-1) in the presence of a palladium catalyst by a method of M. Hard et al. (Liquid Crystals, p741, Vol. 14, No3, 1993) to obtain 5-bromo-2-alkyl-1-ynylpyridine (1-a-2).

Separately, n-butyl lithium etc. is reacted with (1-a-4) which is obtained by protecting a hydroxyl group of 4'-bromo-hydroxybiphenyl (1-a-3) with an appropriate protecting group, to produce an organic lithium reagent. Then the organic lithium reagent is reacted with trimethyl borate in the same reactor and treated with an acid, to obtain a compound (1-a-5) boronic.

Furthermore, 2-(alkyl-1-yl)-5-(4'-substituted biphenyl-4-yl)pyridine (1-a-6) can be obtained by reacting (1-a-2) with (1-a-5) in the presence of a catalyst such as palladium. This is subjected to a hydrogenation reaction in the presence of a hydrogenation catalyst such as palladium on carbon, toobtain 2-alkyl-5-(4'-substituted biphenyl-4-yl)pyridine (1-a-7). 2-alkyl-5-(4'-hydroxybiphenyl-4-yl)pyridine (1-a-8) is obtained by carrying out an appropriate deprotection group reaction on (1-a-7).

Trifluoromethane sulfonate ester (1-a-9) can be obtained by reacting (1-a-8) with anhydrous trifluoromethane sulfonic acid etc. in the presence of a base such as pyridine. 2-alkyl-5(4'-cyanobiphenyl-4-yl)pyridine (1-a-10) can be obtained from the ester for example by the method of M. R. I. Chamber et al. (J. Chem. Soc. Parkin Trans 1, p1361, 1989) with use of potassium cyanide and a nickel catalyst. The pyridine is hydrolyzed by means of a base to produce the corresponding carboxylic acid (1-a-11), from which (1-a) can be obtained by an esterification reaction with an optically active alcohol.

In the case of (1-b), those having the core structure of (1-b) can be prepared preferably by the following steps.

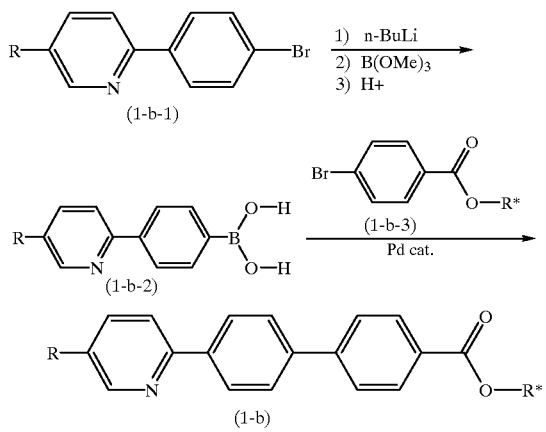

That is, 5-substituted-2-(4-bromophenyl)pyridine (1-b-1) which can be prepared by the method described in Toku-Kai-Sho 60-163864 is reacted with n-butyl lithium etc., to produce an organic lithium reagent. Then, the reagent can be reacted with trimethyl borate and treated with an acid, to obtain a compound (1-b-2) wherein bromine being-substituted with a corresponding boronic acid.

Separately, an optically active 4-bromobenzoate ester (1-b-3) which can be prepared from p-bromobenzoic acid and a corresponding optically active alcohol in a solvent such as methylene chloride with use of a dehydration condensing agent such as dicyclohexyl carbodiimide and the boric acid (1-b-2) are reacted by the cross coupling reaction of Watanabe et al. (Synlet, p7, 1992) with use of a catalyst such as palladium, to prepare a compound expressed by the general formula (1-b).

In the case of (1-c), those having the core structure of (1-c) can be prepared preferably by the following steps.

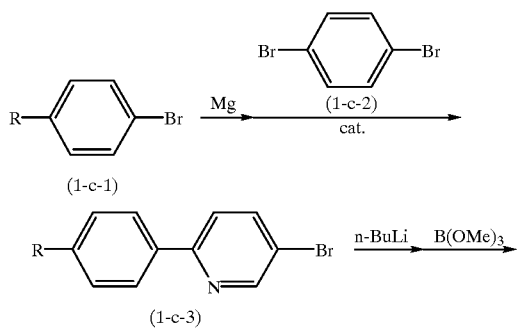

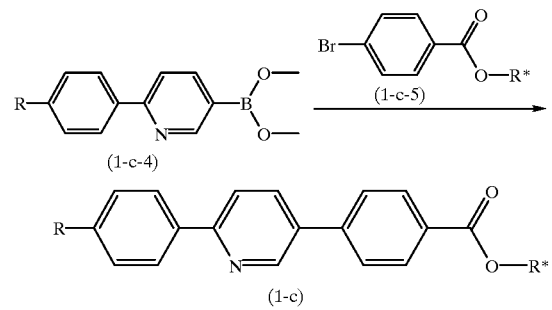

That is, 2,5-dibromopyridine (1-c-2) can be reacted with 4-substituted bromobenzene (1-c-1) as a Grignard reagent in the presence of a catalyst, to prepare 2-(4-substituted phenyl)-5-bromopyridine (1-c-3). This is converted to an organic lithium reagent by means of n-butyl lithium etc., which is then reacted with trimethoxy borate in the same vessel to make a compound (1-c-4) wherein bromine being substituted with a boronic acid. The compound can be reacted with an optically active 4-bromobenzoate ester (1-c-5) which is prepared separately similar to (1-c-3), to prepare (1-c).

In the case of (1-d), those having the core structure of (1-d) can be prepared preferably by the following steps.

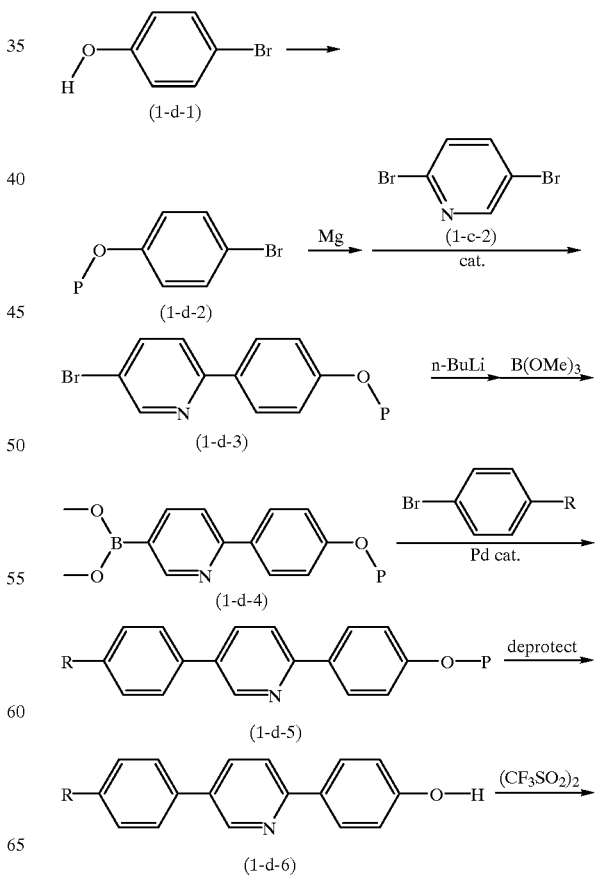

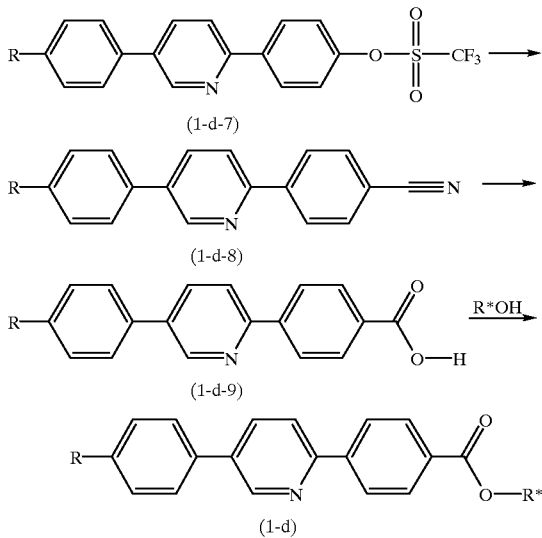

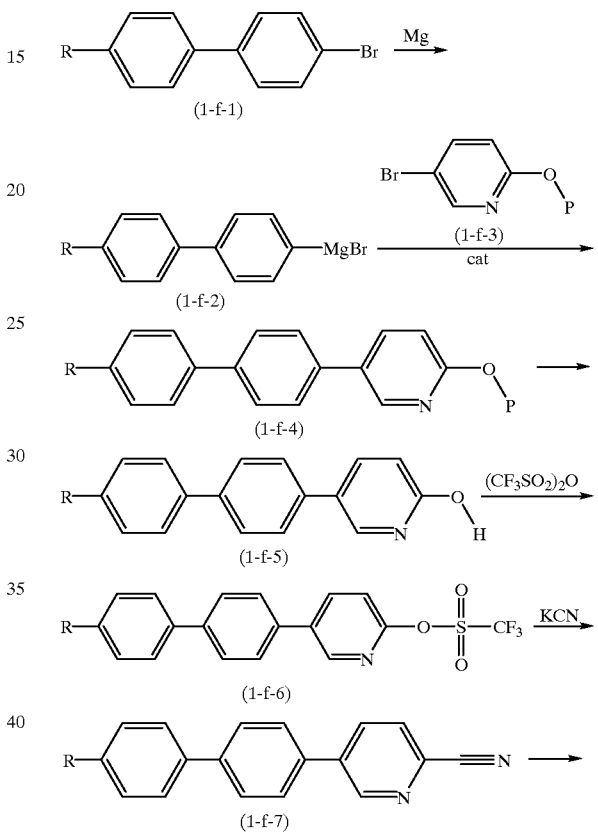

That is, 4'-substituted-4-bromobiphenyl (1-e-1) can be converted to an organic lithium reagent, which can be furthermore reacted with trimethyl borate and treated with an acid to derive a boronic acid (1-e-2). (1-e) can be prepared by a cross coupling reaction with an optically active 6-chloronicotinate ester derivative (1-e-3) separately prepared.

In the case of (1-f), those having the core structure of (1-f) can be prepared preferably by the following steps.

That is, 4-bromophenol (1-d-1) can be protected with an appropriate protecting group to make (1-d-2) as a Grignard reagent, which can be reacted with 2,5-dibromopyridine (1-c-2) in the presence of a palladium catalyst to prepare 2-(4-substituted phenyl)-5-bromopyridine (1-d-3). This can be reacted with n-butyl lithium etc. to make an organic lithium reagent and then reacted with trimethoxy borate in the same vessel, subsequently treated with an acid, to obtain a compound (1-d-4) wherein bromine being substituted with a boric acid.

It is reacted with 4-substituted phenyl bromide in the presence of a catalyst such as palladium to make (1-d-5), which is then subjected to a deprotection treatment by an appropriate method to make phenol (1-d-6).

It is reacted with anhydrous trifluoromethane sulfonic acid etc. to make trifluoromethane sulfonate ester (1-d-7), which is then cyanated to make (1-d-8) and furthermore hydrolyzed to make carboxylic acid (1-d-9), from which (1-d) can be prepared by an esterification reaction with a corresponding optically active alcohol.

In the case of (1-e), those having the core structure of (1-e) can be prepared preferably by the following steps.

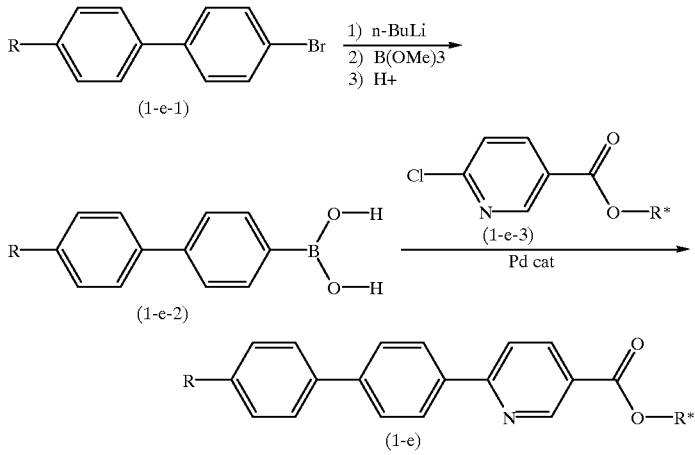

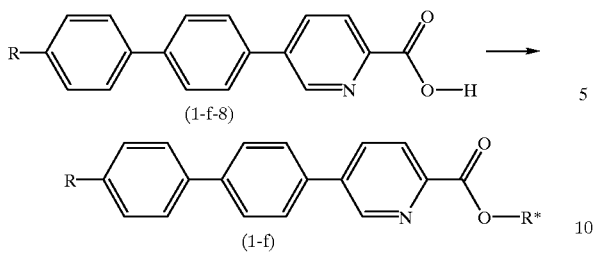

That is, 4'-substituted-4-bromobiphenyl (1-f-1) is converted to a Grignard reagent (1-f-2), which is reacted with (1-f-3) obtained separately from 2-hydroxy-5-bromopyridine having an approximate protecting group in the presence of a catalyst to make (1-f-4), which is then subjected to an appropriate deprotection reaction to make 2-hydroxy-5-biphenyl pyridine (1-f-5). This is converted to a carboxylic acid (1-f-8) via trifluoromethane sulfonylation (1-f-6), cyanation (1-f-7) and hydrolysis.

The desired ester (1-f) can be obtained by reacting the carboxylic acid with a corresponding optically active alcohol.

The backbone structures in which the above-mentioned structures being substituted with fluorine can be preferably prepared by using corresponding starting materials in the above-mentioned methods. Furthermore, they may be prepared by other methods.

It was mentioned above that the optically active sites according to the invention can be classified by the kind of $R_1$ and that they can be preferably prepared from the following optically active starting materials respectively.

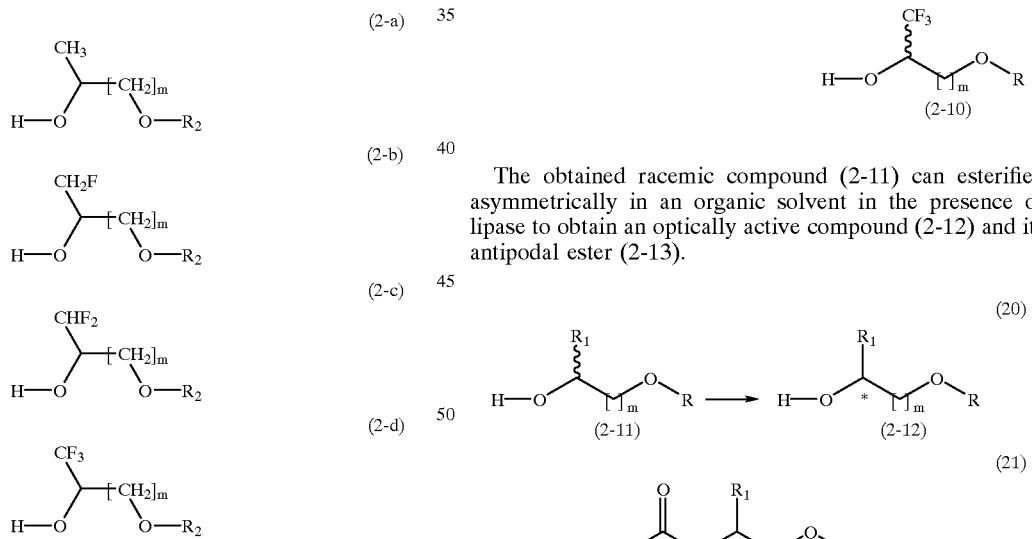

ω-alkoxy-2-alkanol (2-8) or ω-alkoxy-1,1,1-trifluoro-2-alkanol (2-10) which are racemic starting materials for the optically active compounds according to the invention can be prepared by the following methods.

A monobenzyl compound (2-2) of an alkane diol (2-1) is alkylated (2-3), deprotected (2-4), borominated (2-5) and reacted with magnesium to obtain a Grignard reagent (2-6), which is then reacted with acetaldehyde or trifluoroacetate ester to obtain a keton (2-7) or (2-9), which is then reduced with a reducing agent such as sodium borohydride and aluminum lithium hydride to obtain (2-8) or (2-10).

The obtained racemic compound (2-11) can esterified asymmetrically in an organic solvent in the presence of lipase to obtain an optically active compound (2-12) and its antipodal ester (2-13).

An acylating agent which can be used for dividing the racemic compound optically may be an easily available one, more preferably vinyl ester. Examples thereof are vinyl acetate, vinyl propionate, vinyl caproate, vinyl laurate and so on. Furthermore, there may be mentioned enol esters such as isopropenyl acetate and so on similarly. Additionally, triacetin, tripropionin, tributylin, tristearin, trilaurin, trimyristin, triolein and so on may be mentioned as triglycerides. Furthermore, methyl propionate, ethyl acetate, ethyl stearate, trichloroethyl laurate, butyl laurate, ethylene glycol diacetate, anhydrous benzoic acid, anhydrous 1,2-cyclohexane dicarboxylic acid and so on can be used. Any particular treatment is not necessary for them during the reaction.

Operation Effect of the Invention

The first feature of the invention is to exhibit a ferroelectric liquid crystal phase and an antiferroelectric liquid crystal phase in a preferable temperature range. In particular, the antiferroelectric liquid crystal phase is exhibited preferably. By comparing the compounds of the above-mentioned structures (b) and (d) with the compound according to the invention, the latter exhibits the antiferroelectric liquid crystal phase in the wider temperature range from a low temperature such as near the room temperature.

By comparing it with the fact that the compounds of the structures (b) and (d) exhibit the antiferroelectric liquid crystal phases in the range from a temperature somewhat above the room temperature to about 100° C., the liquid crystal temperature range of the compound according to the invention shifts to the more preferable low temperature side. This is a preferable property for preparation of a ferroelectric or antiferroelectric liquid crystalline composition.

Compounds in Example 1
phase transition temperature Cr48 SCA*64.2 SA74.7 Iso

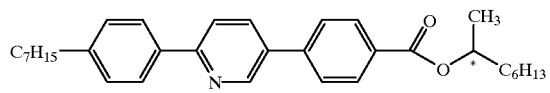

(Comparative Compound A)
phase transition temperature Cr57 SCA*86.7 SC*98.1 SA119.3 Iso

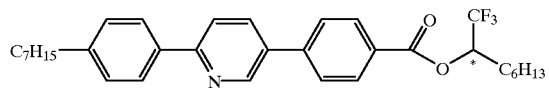

(Comparative Compound B)
phase transition temperature Cr67 CA*81.8 SA93.4 Iso

The second feature of the present invention is low threshold voltage between antiferroelectric state and ferroelectric state by which driving voltage of an antiferroelectric liquid crystal display element being determined.

TABLE 1

| compound | threshold voltage (V/μm) *(temperature) | | | | |
|---|---|---|---|---|---|
| | −5 | −10 | −15 | −20 | −30 |
| Example 1 | 2.1 | 2.3 | — | 1.8 | — |
| Comparative compound A | 2.2 | 3.5 | 4.3 | 5.0 | 6.1 |
| Comparative compound B | 4.4 | 6.7 | — | — | — |

Note. *temperatures are values from upper limit temperature from antiferroelectric liquid crystal phase The compound according to the invention can be used for preparation of a display element with low voltage driving, since the compound has low threshold voltage for transition between ferroelectric state—antiferroelectric state as described above.

Embodiment

The present invention is illustrated in more detail by the following examples.

(Determination of physical properties about ferroelectric and antiferroelectric liquid crystals)

In the examples, determination of physical properties about various ferroelectric and antiferroelectric liquid crystals was carried out as follows.

A spontaneous polarization value (Ps) was obtained by a Sawyer-Tower method, and a tilt angle (θ) was obtained by applying a sufficiently high electric field above the critical electric field on a homogeneously oriented cell, extinguishing a helical structure, reversing polarization and determining a shifting angle (corresponding to 2θ) after extinction under a cross nicol. As a response time, there is adopted a changed time of transparent optical strength in the case of injecting liquid crystals into a cell having an distance of 2 μm between oriented electrodes and applying a short wave form of ±10V/m and 100 Hz.

Whether the liquid crystalline compound exhibits an antiferroelectric property or not is judged by the existence of hysteresis in apparent tilt angle toward an applied voltage curve during electrooptical response of a liquid crystal element and the appearance of three state switching in electrooptical response. For determination of the threshold voltage of the compound and the composition in the case of antiferroelectric property being present, one in a set of substrates having coated polyimide type alignment film on a glass substrate equipped with a transparent electrode is subjected to rubbing treatment and placed opposed to other one, and then liquid crystals are injected into a cell with an electrode distance controlled to 5 μm at a high temperature.

The compound was cooled gradually until an antiferroelectric liquid crystal phase (SCA* phase) being obtained, to prepare a liquid crystal display element with an uniform alignment. As the threshold voltage of transition owing to electric field application of a phase between antiferroelectric phase and ferroelectric phase, there is adopted an applied voltage at which clear phase transition being observed by biphenomenal oscilloscope of optical response and applied voltage in the case of applying triangle wave with 50 mHz into liquid crystal cells.

Preparation of optically active starting material
Preparation of (+) -7-ethoxy-1,1,1-trifluoro-2-heptanol
The first step A solution of 194 g (1 mol) of pentanediol monobenzyl ether in 1 L of tetrahydrofuran (hereinafter referred to THF) was added to a solution of 48 g (2 mol) of sodium hydride in 100 ml of THF under cooling. Then, the mixture was heated under reflux for 2 hours and cooled to the room temperature before 140 g (1.3 mol) of ethyl bromide in 300 ml of THF was added dropwise. The mixture was heated under reflux for 6 hours. 500 ml of water was added and extraction was carried out with 500 ml of diethyl ether. After the organic layer was neutralized and washed with water and dried over anhydrous magnesium sulfate and concentrated. The oily residue was purified by distillation under the reduced pressure, to obtain 192 g of pentanediol benzyl ethyl ether. Boiling point; 110–117° C. (1 mmHg).

The second step

A solution of 90 g (0.4 mol) of pentanediol benzyl ethyl ether and 5.7 g of palladium hydroxide on carbon in 500 ml of ethanol was hydrogenated at under the pressure. After removing off the catalyst by filtration, the reaction mixture was concentrated. The oily residue was purified by distillation under the reduced pressure, to obtain pentanediol monoethyl ether. Boiling point; 55–58° C. (0.3 mmHg).

The third step 10 g of pyridine was added dropwise to a solution of 78 g (0.29 mol) of phosphorus tribromide in 130 ml of benzene. After the solution was stirred for 10 minutes and cooled to −5° C., a mixture of 102 g (0.77 mol) of pentane diol monoethyl ether and 5 g of pyridine was added dropwise. After maintaining the reaction temperature at 0° C. and stirring for 2 hours, the solution was stirred for 8 hours at the room temperature. 100 ml of water was added and extracted with diethyl ether. The organic layer was washed subsequently with 6N hydrochloric acid and an aqueous sodium hydrogen carbonate solution, then dried over anhydrous magnesium sulfate and concentrated. The residue was distilled under the reduced pressure, to obtain 103 g of 5-bromopentyl ethyl ether. Boiling point; 47–48° C. (1 mmHg).

The fourth step

A Grignard reagent which was prepared from 6.4 g (0.27 mol) of magnesium turnings and 48.7 g (0.25 mol) of 5-bromopentyl ethyl ether was added over 45 minutes to a solution of 35.5 g (0.25 mol) of ethyl trifluoroacetate in 300 ml of diethyl ether at –60° C. After stirring for further 2 hours, the temperature was increased to –20° C. and a saturated aqueous ammonium chloride solution was added. The organic layer was washed with water, dried over anhydrous magnesium sulfate and concentrated. The residue was distilled under the reduced pressure, to obtain 31 g of 7-ethoxy-1,1,1-trifluoro-2-heptanone. Boiling point; 90–92° C. (47 mmHg).

The fifth step 2.6 g (0.07 mol) of sodium borohydride was added gradually to a solution of 30 g (0.14 mol) of 7-ethoxy-1,1,1-trifluoro-2-heptanone in 200 ml of ethanol at 0° C. The solution was stirred for 24 hours at room temperature. 200 ml of water was added and extracted with diethyl ether. The organic layer was washed with a small amount of water, dried over anhydrous magnesium sulfate and concentrated. The residue was distilled under the reduced pressure, to obtain 28 g of racemic 7-ethoxy-1,1,1-trifluoro-2-heptanol. Boiling point; 133–137° C. (50 mmHg).

The sixth step 5.17 g (0.060 mol) of vinyl acetate and 3.0 g of lipase (Nobozyme 435, manufactured by Nobonordisc Co.) were added subsequently to a solution of 21.4 g (0.1 mol) of racemic 7 -ethoxy-1,1,1-trifluoro-2-heptanol in 50 ml of heptane and stirred for 4 days at 35° C. Lipase was removed from the reaction mixture by filtration. The filtrate was concentrated and the residue was purified by silica gel column chromatography (heptane/ethyl acetate=10/1 (v/v)), to obtain 8.17 g of (+)-7-ethoxy-1,1,1-trifluoro-2-heptanol and 10.57 g of (–)-2-(7-ethoxy-1,1,1-trifluoroheptyl) acetate. The specific optical rotation of(+)-7-ethoxy-1,1,1-trifluoro-2-heptanol was as follows:

$[\alpha]D^{26}$+14.93 (c1.147, CHCl$_3$).

The seventh step 10.81 g of (+)-7-ethoxy-1,1,1-trifluoro-2-heptanol obtained in the six step was dissolved in 30 ml of heptane, to which 2.58 g (0.030 mol) of vinyl acetate and 3.0 g of lipase used in Example 1, the six step were added subsequently and stirred for 6 days at 35° C. The reaction mixture was filtered to remove lipase. The filtrate was concentrated under the reduced pressure and the residue was purified by silica gel column chromatography (heptane/ethyl acetate 10/1 (v/v)), to obtain 7.31 g of (+) -7-ethoxy-1,1,1-trifluoro-2-heptanol. It was MTPA esterified by the general method and analyzed by gas chromatography to be determined as 95.2%ee.

EXAMPLE 1

Preparation of (R)-(1-trifluoromethyl-6-ethoxy)hexyl 4-(2-(4-heptylphenyl)pyridin-5-yl) bezoate ester (The first step)

23 g (98 mmol) of 2,5-dibromopyridine and 0.57 g (0.5 mmol) of tetrakis triphenyl phosphine palladium (0) (hereinafter referred to Pd(TPP)$_4$) were added to 200 ml of a Grignard reagent which was prepared from 2.3 g (98 mmol) of magnesium turnings and 25 g (98 mmol) of p-heptylbromobenzene and heated under reflux for 2 hours.

After cooling, extraction was carried out with diethyl ether. The organic layer was washed with an aqueous ammonium chloride solution and water, dried over anhydrous magnesium sulfate and concentrated. The residue was purified by column chromatography, to obtain 35 g of 5-bromo-2-(4-heptylphenyl) pyridine.

(The second step)

7 ml of n-butyl lithium (1.69 mol/l of hexane solution) was added dropwise to a solution of 34 g (0.1 mol) of 5-bromo-2-(4-heptylphenyl)pyridine in 100 ml of THF cooled to –60° C. After stirring for 1 hour with maintaining at –60° C., 3 g of trimethyl borate was added dropwise and stirred for further 1 hour. After the inner temperature was returned gradually to the room temperature, 40 ml of 6N hydrochloric acid was added, and then THF was distilled off. The obtained solid was filtered and recrystallized, to obtain 30 g of pyridine 2-(heptylphenyl)-5-boronic acid.

(The third step)

2.6 g (0.18 mol) of dicyclohexyl carbodiimide (hereinafter abbreviated as DCC) and 0.1 g of 4-dimethylamino pyridine (hereinafter abbreviated as DMAP) were added to a solution of 2 g (1 mmol) of p-bromobenzoic acid and 2.1 g (10 mmol) of (+)-7-ethoxy-1,1,1-trifluoro-2-heptanol in dichloromethane and stirred for 24 hours at the room temperature. The formed insolubles were removed from the reaction solution by filtration and the filtrate was extracted with toluene. The organic layer was washed with water, dried over anhydrous sodium sulfate and concentrated. The residue was purified by column chromatography, to obtain 3.1 g of (R)-(1-trifluoromethyl-6-ethoxy)hexyl 4-bromobenzoate ester.

(The fourth step)

A mixed solution of 0.7 g (10 mmol) of pyridine 2-(heptylphenyl)-5-boronic acid, 1 g (2.5 mmol) of (R)-(1-trifluoromethyl-6-ethoxy)hexyl 4-bromobenzoate ester, 0.3 g of sodium carbonate, 0.06 g of Pd(TPP)$_4$, 12 ml of dimethoxyethane and 2 ml of water was refluxed for 8 hours with stirring. The reaction solution was extracted with toluene. The organic layer was dried over anhydrous magnesium sulfate and concentrated. The residue was purified by column chromatography (toluene). The effluent was concentrated and recrystallized from ethanol, to obtain 0.3 g of (R)-(1-trifluoromethyl-6-ethoxy) hexyl 4-(2-(4-heptylphenyl) pyridin-5-yl) benzoate ester. The said compound has the following phase transition point;

Cr48 SCA*64.2 SA74.7 Iso.

EXAMPLE 2

Preparation of (1-trifluoromethyl-6-ethoxy)hexyl 4'-(5-heptylpyridin-2-yl) biphenyl-4-yl carboxylate ester (The first step)

9 ml of n-butyl lithium (1.68M hexane solution) was added dropwise to a solution of 5 g of 5-heptyl-2-(4-bromophenyl) pyridine prepared by the method described in Toku-Kai-Sho 60-163864 in 100 ml of THF with maintaining at –60° C. After stirring for 30 minutes with maintaining at –60° C., 3 g of trimethyl borate was added and stirred for further 1 hour. After the inner temperature was recovered gradually to the room temperature, 40 ml of 6N hydrochloric acid was added and then THF was distilled off. The formed solid was filtered and recrystallized, to obtain 3 g of 4-(5-heptylpyridin-2-yl)phenyl boronic acid. Melting point; 206–214° C.

(The second step)

37 g (0.18 mol) of DCC and 0.02 g (0.15 mol) of DMAP were added to a solution of 30.1 g (0.15 mol) of p-bromobenzoic acid and 19.5 g (0.15 mol) of 7-ethoxy-1,1,1-trifluoro-2-heptanol in dichloromethane and stirred for 24 hours at the room temperture. The formed insolubles were removed off by filtration and the filtrate was extracted with toluene. The organic layer was washed with water, dried over anhydrous sodium sulfate and concentrated. The residue was purified by column chromatography, to obtain 32 g of (1-trifluoromethyl-6-ethoxy)hexyl 4-bromobenzoate ester. The said compound has the following $^1$H-NMR data;
$^1$H-NMR (CDCl$_3$) δ0.98(3H, t), 1.20–1.60(m), 1.60–1.90 (m), 5.20(1H, q), 7.63(2H, d), 7.97(2H, d).
(The third step)
A mixed solution of 0.5 g (1.7 mmol) of 4-(5-heptylpyridin-2-yl)phenyl boronic acid, 0.52 g (1.6 mmol) of (1-trifluoromethyl-6 -ethoxy)hexyl 4-bromobenzoate ester, 0.3 g of sodium carbonate, 0.05 g of Pd(TPP)$_4$, 12 ml of dimethoxyethane (hereinafter abbreviated as DME) and 2 ml of wter was heated and stirred for 8 hours. The reaction solution was extracted with toluene. The organic layer was dried over anhydrous magnesium sulfate and concentrated. The residue was purified by column chromatography (toluene) and recrystallized from ethanol, to obtain 0.3 g of (1-trifluoromethyl-6-ethoxy)hexyl 4'-(5-heptylpyridin-2-yl) biphenyl-4-yl carboxylate ester. The said compound has the following phase transition point;
Cr-SX46 SCA*76.7 Iso.
The said compound was in liquid crystalline state at the room temperature, so that the melting point thereof could not be measured.

EXAMPLE 3
Preparation of (1-trifluoromethyl-6-ethoxy)hexyl 4'-(5-heptylpyridin-2-yl) 3,5-difluoro-biphenyl-4-yl carboxylate ester
(The first step)
1 g of 5-heptyl-2-(3',5'-difluoro-4-biphenyl)pyrigin was prepared from 3,5-difluorobromobenzene and 4-(5-heptylpyridin-2-yl)phenyl boric acid by the similar method to Example 1, the third step. The said compound exhibits a liquid crystal phase and has the following phase transition point;
Sc122 Iso from the room temperature.
(The second step)
1.6 ml of n-butyl lithium (1.68 mol hexane solution) was added dropwise to a solution of 1 g (2.7 mol) of 5-heptyl-2-(3',5'-difluoro-4-biphenyl)pyridine in 20 ml of THF cooled to −60° C. After the addition being completed, stirring at −60° C. was continued for 30 minutes and 1 g of dry ice was introduced and stirred for 1 hour. Then, the temperatuer within the system was returned to the room temperature and stirred for one night. By adding 30 ml of 6N hydrochloric acid and stirring, crystals were precipitated. Crystals were collected by filtration, dried and recrystallized from acetic aced, to obtain 0.6 g of 4'-(5-heptylpyridin-2-yl)-3,5-difluorobiphenyl)-4-carboxylic acid. The compound has a melting point of 185–186° C.
(The third step)
0.30 g (0.73 mmol) of 4'-(5-heptylpyridin-2-yl)-3,5-difluorobiphenyl)-4-carboxylic acid was dissolved in 20 ml of dimethylformamide (hereinafter abbreviated as DMF), then 0.12 g (0.74 mmol) of carbonyl diimidazole (hereinafter abbreviated as CDI) was added and stirred for 2 hours with maintaining the inner temperature at 40° C.
To the reaction solution, a solution obtained separately by adding 0.1 g (0.76 mmol) of 7-ethoxy-1,1,1-trifluoro-2-heptanol and 0.036 g (1.52 mmol) of sodium hydride and refluxing for 2 hurs was added dropwise and heated under reflux for 5 hours. 30 ml of water was added and extracted with toluene. The organic layer was dried over anhydrous magnesium sulfate.
Concentrated residue was purified by column chromatography (toluene) and recrystllized from ethanol, to obtain (1-trifluoromethyl-6-ethoxy)hexyl 4'-(5-heptylpyridin-2-yl)-3,5-difluoro-biphenyl-4-yl carboxylate ester.

EXAMPLE 4
(1-trifluoromethyl-6-ethoxy)hexyl (4'-(2-heptylpyridin-5-yl) biphenyl-4-yl carboxylate ester (The first step)
17.2 g (0.18 mol) of 1-heptyne was dissolved in THF, and the reaction solution was cooled to 0° C. Thereto, 128 ml of n-butyl lithium (1.56M hexane solution) was added dropwise for 15 minutes. After stirring for further 30 minutes, a (0.5M) solution of zinc chloride in 400 ml of THF was added dropwise for minutes. The reaction temperature was raised to 20° C. for 30 minutes. Thereto, 2.5 g of Pd(TPP)$_4$ and 37 g (0.16 mol) of 2,5-dibromopyridine were added and stirred for 2 days at the room temperature.
200 ml of water was added to the reaction mixture, extracted with ethyl acetate. The organic layer was dried over anhydrous magnesium sulfate. It was concentrated and recrystallized, to obtain 41.8 g of 2-(1-heptynyl)-5-bromopyridine.
Melting point; 141–143° C.
The said compound has the following $^1$H-NMR data;
$^1$H-NMR (CDCl$_3$) δ 0.91(3H, t), 1.10–1.60(m), 2.10(2H, t), 7.30(1H,dd), 8.00(1H,dd), 9.26(1H,d).
(The second step)
5.9 g of 2-(1-heptynyl)-5-(4'-methoxymethoxy-4-biphenyl) pyridine was obtained by using 14.7 g (58.3 mmol) of 2-(1-heptynyl)-5-bromopyridine, 15 g (58.3 mmol) of 4-methoxymethoxy-4'-biphenyl boronic acid, 10 g of sodium carbonte, 1.3 g (1.13 mmol) of Pd(TPP)$_4$, 2.4 g (5.6 mmol) of lithium chloride, 500 ml of DME and 40 ml of water by similar operation to Example 1, the third step.
Melting point; 182° C.
The said compound has the following $^1$H-NMR data;
$^1$H-NMR (CDCl$_3$) δ 0.92 (3H, t), 1.20–1.28 (6H,m), 2.38 (2H, t), 3.49 (3H, s), 5.21 (2H, s), 7.00–7.25(m), 7.25–7.90 (m), 8.81 (1H, d)
(The third step)
To a solution of 4.8 g (12.5 mmol) of 2-(1-heptynyl)-5-(4'-methoxymethoxy-4-biphenyl) pyridine and 1.2 g of palladium on carbon in 150 ml of ethyl acetate was hydrogenated at the normal pressure. Palladium on carbon was removed by filtration, and concentrated to obtain 4.9 g of 2-heptyl-5-(4'-methoxymethoxy-4-biphenyl) pyridine. It has the melting point of 188° C.
The said compound has the following $^1$H-NMR data;
$^1$H-NMR (CDCl$_3$) δ 0.92 (3H, t), 1.20–1.28 (6H,m), 1.28–1.95 (2H,m), 2.84 (2H, t), 3.49(31H,s), 5.21(2H,s), 7.00–7.25(m), 7.25–7.90(m), 8.81(1H,d).
(The fourth step)
A solution of 4.9 g (15.1 mmol) of 2-heptyl-5-(4'-methoxymethoxy-4-biphenyl)pyridine, 5.5 g (36.9 mmol) of sodium iodide and 2 g of 12N hydrochloric acid in 150 ml of acetone was heated under reflux for 3 hours. After distilling off acetone, an aqueous sodium hydroxide was added to neutralize the reaction solution and then extraction was carried out with ethyl acetate. The organic layer was dried over anhydrous sodium sulfate and concentrated, to obtain crystals. These were recrystallized from ethanol, to obtain 4.5 g of 2-heptyl-5-(4'-hydroxy-4-biphenyl) pyridine.
The said compound has the following $^1$H-NMR data;
$^1$H-NMR (CDCl$_3$) δ 0.92 (3H, t), 1.10–1.60 (H,m), 1.60–1.98 (2H,m), 2.84 (2H, t), 6.91–7.01(m), 7.21–8.10 (m), 8.78 (1H,d).
(The fifth step)
3.6 g (13.0 mmol) of anhydrous trifluoromethane sulfonic acid was added dropwise to a solution of 4.2 g (12.0 mmol) of 2-heptyl-5-(4'-hydroxy-4-biphenyl)pyridine in 30 ml of pyridine cooled to 5° C. After stirring at the room temperature for 2 days, the reaction solution was poured on 50 ml of ice water and extraction was carried out with 200 ml of ether. The organic layer was washed subsequently with a 3% aqueous hydrochloric acid solution and a saturated sodium hydrogen carbonate and dried over anhydrous sodium sulfate. After concentration, it was purified by silica gel column chromatography, to obtain 2.7 g of 4'-(2-heptylpyridin-5-yl) biphenyl-4-yl trifluoromethane sulfonate.

The said compound has the following $^1$H-NMR data;
$^1$H-NMR (CDCl$_3$) δ 0.92 (3H, t), 1.20–1.28 (H, m), 1.28–1.95 (2H,m), 2.84 (2H,t), 7.19–7.41(m), 7.60–7.90(m), 8.81 (1H, d).

(The sixth step)

A solution of 2.0 g (4.2 mmol) of 4'-(2-heptylpyridin-5-yl) biphenyl-4-yl trifluoromethane sulfonate, 0.5 g (9.0 mmol) of potassium cyanide, 0.15 g (0.2 mmol) of bis (triphenylphosphine) nickel bromide, 0.1 g (1.2 mmol) of zinc powders and 0.1 g of triphenylphosphine in 2.5 ml of acetonitrile was heated under reflux for 6 hours. 10 ml of water was added and extraction was carried out with 50 ml of ethyl acetate. The organic solution was purified by silica gel column chromatography, to obtain 0.5 g of 4'-(2-heptylpyridin-5-yl)-4-cyanobiphenyl.

The said compound has the following $^1$H-NMR data;
$^1$H-NMR (CDCl$_3$) δ 0.92(3H,t), 1.20–1.40(H,m), 1.40–1.95(2H,m), 2.84(2H,t), 7.19–7.41(m), 7.60–7.90(m), 8.81 (1H, d).

(The seventh step)

0.5 g (1.4 mmol) of 4'-(2-heptylpyridin-5-yl)-4-cyanobiphenyl and 0.5 g of sodium hydroxide were added to 20 ml of diethylene glycol and refluxed for 12 hours. By adding 200 ml of a 3% aqueous hydrochloric acid solution to the reaction solution, crystals were precipitated, separated by filtration and dried with air. The solid was recrystallized from acetic acid, to obtain 0.5 g of 4'-(2-heptylpyridin-5-yl)-4-biphenyl carboxylic acid. The melting thereof was above 250° C.

(The eighth step)

(1-trifluoromethyl-6-ethoxy)hexyl 4'-(2-heptylpyridin-5-yl) biphenyl-4-yl carboxylate ester was obtained by esterifyng 4'-(2-heptylpyridin-5-yl)-4-biphenyl carboxylic acid with 7-ethoxy-1,1,1-trifluoro-2-heptanol by the similar operation to Example 3, the third step.

EXAMPLE 5

Physical properties of the compound in Example 1 as ferroelectric liquid crystals was measured according to the above-mentioned methods.

| T(° C.) | Ps(nc/cm$^2$) | Tilt angle (°) |
|---|---|---|
| 60.0 | 192.3 | 23.7 |
| 50.0 | 294.3 | 29.1 |
| 40.0 | 347 | 31.3 |

Thus, the compound exhibits very high spontaneous polarization together with a large tilt angle, which can be used very preferably as ferroelectric liquid crystals.

EXAMPLE 6

(determination of physical properties of antiferroelectric liquid crystals)

Physical properties of antiferroelectric liquid crystals of the compound in Example 1 were measured.

Threshold characteristics of antiferroelectric properties at various temperatures are shown as follows.

| T-Tc | V (Voltage) |
|---|---|
| −5 | 2.1 |
| −10 | 2.3 |
| −20 | 1.8 |

EXAMPLE 7

(Example of antiferroelectric liquid crystalline composition)

The following liquid crystalline compositions were prepared by using the compound prepared in Example 1.

| | |
|---|---|
| 2-(4-hexyloxyphenyl)-5-octylpyridine | 28.5 wt % |
| 2-(4-octyloxyphenyl)-5-octylpyridine | 19.0 wt % |
| 2-(4-nonyloxyphenyl)-5-octylpyridine | 9.5 wt % |
| 2-(4-decyloxyphenyl)-5-octylpyridine | 9.5 wt % |
| 2-(4'-pentyl-4-biphenyl)-5-octylpyridine | 19.0 wt % |
| 2-(4'-heptyl-4-biphenyl)-5-octylpyridine | 9.5 wt % |
| the compound in Example 1 | 5.0 wt % |

The liquid crystal phase transition temperature (° C.) of the composition was as follows;

SC*51.5° C. SA83.1° C. N*88.9° C. Iso

Furthermore, the physical properties of ferroelectric liquid crystals at various temperatures are shown in the following table.

TABLE 2

| T(° C.) | Ps(nC/cm$^2$) | θ (°) | τ (μsec) |
|---|---|---|---|
| 40 | 2.0 | 12.1 | 46 |
| 30 | 2.6 | 13.8 | 71 |
| 25 | 2.8 | 14.4 | 92 |
| 20 | 3.0 | 14.7 | 120 |

(Example of antiferroelectric liquid crystalline composition)

The equal amount mixture of the compound in Example 1 and the following compound was prepared.

(R)

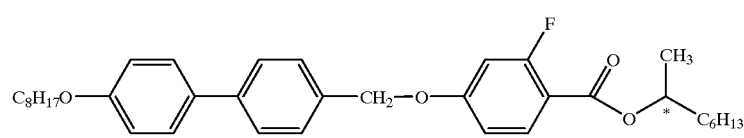

The liquid crystal phase transition temperature (° C.) of the composition was as follows;

SCA*63.7° C. SA83.6° C. Iso

Furthermore, threshold voltages of antiferroelectric liquid crystals are shown in the following table.

TABLE 3

| T(° C.) | Vth(V) |
|---|---|
| 58.7 | 2.6 |
| 53.7 | 3.7 |
| 48.7 | 3.9 |
| 43.7 | 4.4 |
| 30.0 | 3.8 |
| 25.0 | 3.6 |
| 20.0 | 3.7 |

What is claimed is:

1. A compound expressed by the general formula (1)

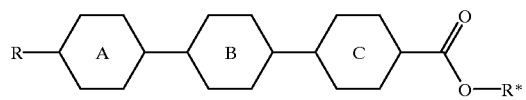

wherein, either one of rings A, B and C denotes

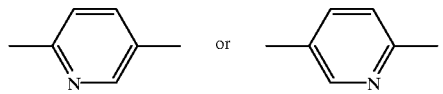

remaining two of them denote each independently

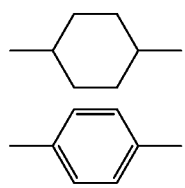

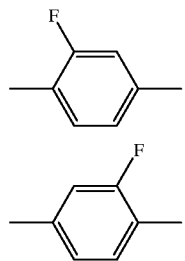

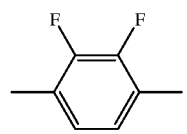

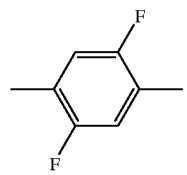

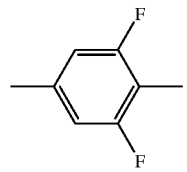

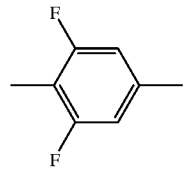

R denotes an alkyl group or an alkoxy group with 4–16 carbon atoms, and

R* denotes

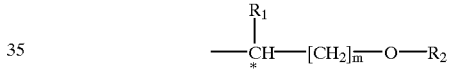

in which, $R_1$ denotes $CH_3$, $CF_3$, $CH_2F$ or $CHF_2$, $R_2$ denotes an alkyl group with 1–10 carbon atoms and m denotes 2–12.

2. A liquid crystalline composition containing at least one compound according to claim 1.

3. A liquid crystal element which is constructed by using a liquid crystalline composition containing at least one compound according to claim 1.

* * * * *